(12) United States Patent
Dong et al.

(10) Patent No.: US 10,167,336 B2
(45) Date of Patent: *Jan. 1, 2019

(54) METHODS AND MATERIALS FOR TREATING CANCER

(71) Applicant: Mayo Foundation for Medical Education and Research, Rochester, MN (US)

(72) Inventors: Haidong Dong, Rochester, MN (US); Eugene D. Kwon, Rochester, MN (US); Svetomir N. Markovic, Rochester, MN (US); Christopher J. Krco, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 218 days.

This patent is subject to a terminal disclaimer.

(21) Appl. No.: 15/054,385

(22) Filed: Feb. 26, 2016

(65) Prior Publication Data

US 2016/0176967 A1   Jun. 23, 2016

Related U.S. Application Data

(63) Continuation of application No. 14/192,376, filed on Feb. 27, 2014, now Pat. No. 9,302,005.

(60) Provisional application No. 61/786,199, filed on Mar. 14, 2013.

(51) Int. Cl.
| | |
|---|---|
| C07K 16/28 | (2006.01) |
| A61K 39/395 | (2006.01) |
| A61K 45/00 | (2006.01) |
| C07K 14/705 | (2006.01) |
| C12N 15/113 | (2010.01) |
| A61K 35/17 | (2015.01) |

(52) U.S. Cl.
CPC .......... *C07K 16/2803* (2013.01); *A61K 45/00* (2013.01); *C07K 14/70532* (2013.01); *C12N 15/1138* (2013.01); *A61K 35/17* (2013.01); *C07K 2317/76* (2013.01); *C07K 2319/00* (2013.01); *C12N 2310/14* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |
| 4,769,330 A | 9/1988 | Paoletti et al. |
| 4,816,567 A | 3/1989 | Cabilly et al. |
| 4,861,627 A | 8/1989 | Mathiowitz et al. |
| 4,861,719 A | 8/1989 | Miller |
| 4,925,673 A | 5/1990 | Steiner et al. |
| 4,935,496 A | 6/1990 | Kudo et al. |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |
| 5,225,336 A | 7/1993 | Paoletti |
| 5,225,538 A | 7/1993 | Capon et al. |
| 5,235,033 A | 8/1993 | Summerton et al. |
| 5,240,846 A | 8/1993 | Collins et al. |
| 5,254,678 A | 10/1993 | Haseloff et al. |
| 5,278,056 A | 1/1994 | Bank et al. |

(Continued)

FOREIGN PATENT DOCUMENTS

| | | |
|---|---|---|
| EP | 1 074 617 | 2/2001 |
| EP | 1 537 878 | 6/2005 |

(Continued)

OTHER PUBLICATIONS

U.S. Appl. No. 15/019,457, filed Feb. 9, 2016, 20160153996, Jun. 2, 2016, Kwon et al.
U.S. Appl. No. 15/019,548, filed Feb. 9, 2016, 20160154000, Jun. 2, 2016, Kwon et al.
U.S. Appl. No. 15/026,461, filed Sep. 1, 2016, 20160251437, Sep. 1, 2016, Dong et al.
U.S. Appl. No. 15/311,552, filed Nov. 16, 2016, 20170089918, Mar. 20, 2017, Dong.
U.S. Appl. No. 15/325,612, filed Jan. 11, 2017, 20170173030, Jun. 22, 2017, Dong.
U.S. Appl. No. 15/692,656, filed Aug. 31, 2017, Kwon et al.
Ahmadzadeh et al., "Tumor antigen-specific CD8 T cells infiltrating the tumor express high levels of PD-1 and are functionally impaired," *Blood*, 114(8):1537-1544, Epub May 7, 2009.
Anikeeva et al., "Distinct role of lymphocyte function-associated antigen-1 in mediating effective cytolytic activity by cytotoxic T lymphocytes," *Proc Natl Acad Sci U S A.*, 102(18):6437-6442, Epub Apr. 25, 2005.

(Continued)

*Primary Examiner* — Ilia I Ouspenski
(74) *Attorney, Agent, or Firm* — Fish & Richardson P.C.

(57) ABSTRACT

This document provides methods and materials involved in treating cancer. For example, methods and materials for identifying a mammal as having an elevated level of PD-1$^+$/CD11a$^{high}$ CD8 T cells having the potential to exert anti-cancer effects are provided. In addition, methods and materials for identifying a mammal as having an elevated level of PD-1$^+$/CD11a$^{high}$ CD8 T cells and administering a PD-1 inhibitor to such a mammal are provided.

12 Claims, 9 Drawing Sheets

(56) References Cited

U.S. PATENT DOCUMENTS

| | | |
|---|---|---|
| 5,284,656 A | 2/1994 | Platz et al. |
| 5,296,347 A | 3/1994 | LaMotte, III |
| 5,391,682 A | 2/1995 | Ogawa et al. |
| 5,451,569 A | 9/1995 | Wong et al. |
| 5,502,167 A | 3/1996 | Waldmann et al. |
| 5,521,288 A | 5/1996 | Linsley et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,584 A | 10/1996 | Sledziewski et al. |
| 5,585,089 A | 12/1996 | Queen et al. |
| 5,596,086 A | 1/1997 | Matteucci et al. |
| 5,639,641 A | 6/1997 | Pedersen et al. |
| 5,674,704 A | 10/1997 | Goodwin et al. |
| 5,675,848 A | 10/1997 | Kappel |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,714,147 A | 2/1998 | Capon et al. |
| 5,733,743 A | 3/1998 | Johnson et al. |
| 5,750,078 A | 5/1998 | Shitara et al. |
| 5,750,375 A | 5/1998 | Sledziewski et al. |
| 5,750,666 A | 5/1998 | Caruthers et al. |
| 5,770,403 A | 6/1998 | Dalie et al. |
| 5,843,725 A | 12/1998 | Sledziewski et al. |
| 5,861,310 A | 1/1999 | Freeman et al. |
| 5,874,240 A | 2/1999 | Ni et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aruffo et al. |
| 6,291,212 B1 | 9/2001 | Sledziewski et al. |
| 6,291,646 B1 | 9/2001 | Sledziewski et al. |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,891,030 B2 | 5/2005 | Chen |
| 6,919,193 B2 | 7/2005 | Tang et al. |
| 6,943,150 B1 | 9/2005 | Altieri |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,449,300 B2 | 11/2008 | Chen et al. |
| 7,560,540 B2 | 7/2009 | Pardoll et al. |
| 7,563,869 B2 | 7/2009 | Honjo et al. |
| 7,582,439 B2 | 9/2009 | Cory et al. |
| 7,595,048 B2 | 9/2009 | Honjo et al. |
| 7,651,686 B2 | 1/2010 | Chen et al. |
| 7,709,214 B2 | 5/2010 | Freeman et al. |
| 7,723,479 B2 | 5/2010 | Mikesell et al. |
| 7,794,710 B2 | 9/2010 | Chen et al. |
| 7,892,540 B2 | 2/2011 | Chen et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,163,550 B2 | 4/2012 | Chen et al. |
| 8,268,635 B2 | 9/2012 | Ferrante et al. |
| 8,273,864 B2 | 9/2012 | Chen |
| 8,460,927 B2 | 6/2013 | Chen |
| 8,772,026 B2 | 7/2014 | Chen et al. |
| 8,981,063 B2 | 3/2015 | Chen |
| 9,302,005 B2 * | 4/2016 | Dong .................... A61K 45/00 |
| 2002/0076409 A1 | 6/2002 | March et al. |
| 2002/0091246 A1 | 7/2002 | Pardoll et al. |
| 2002/0095024 A1 | 7/2002 | Mikesell et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0119121 A1 | 8/2002 | Vitiello et al. |
| 2002/0160395 A1 | 10/2002 | Altieri et al. |
| 2002/0160973 A1 | 10/2002 | Pero et al. |
| 2002/0164600 A1 | 11/2002 | Freeman et al. |
| 2002/0168719 A1 | 11/2002 | Kwon |
| 2002/0177551 A1 | 11/2002 | Terman |
| 2003/0039653 A1 | 2/2003 | Chen et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0223989 A1 | 12/2003 | Pluenneke |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0180047 A1 | 9/2004 | Chen |
| 2004/0247563 A1 | 12/2004 | Lynch et al. |
| 2005/0013811 A1 | 1/2005 | Chen et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0068386 A1 | 3/2006 | Slesarev et al. |
| 2006/0084794 A1 | 4/2006 | Rosen et al. |
| 2006/0110383 A1 | 5/2006 | Honjo et al. |
| 2006/0159685 A1 | 7/2006 | Mikesell et al. |
| 2006/0223088 A1 | 10/2006 | Rosen et al. |
| 2006/0276422 A1 | 12/2006 | Usman et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0042292 A1 | 2/2009 | Chen |
| 2009/0068193 A1 | 3/2009 | Chen et al. |
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0304711 A1 | 12/2009 | Pardoll et al. |
| 2010/0015642 A1 | 1/2010 | Kwon et al. |
| 2010/0285039 A1 | 11/2010 | Chen |
| 2011/0020325 A1 | 1/2011 | Kwon et al. |
| 2011/0010409 A1 | 5/2011 | Strome et al. |
| 2012/0065374 A1 | 3/2012 | Pardoll et al. |
| 2012/0065385 A1 | 3/2012 | Pardoll et al. |
| 2012/0225043 A1 | 9/2012 | Chen et al. |
| 2013/0058936 A1 | 3/2013 | Bruenker et al. |
| 2013/0123566 A1 | 5/2013 | Lupold et al. |
| 2013/0251736 A1 | 9/2013 | Kwon et al. |
| 2013/0273656 A1 | 10/2013 | Hendrickson |
| 2014/0031260 A1 | 1/2014 | O'Donnel et al. |
| 2014/0242080 A1 | 8/2014 | Roche |
| 2014/0271674 A1 | 9/2014 | Dong |
| 2014/0329248 A1 | 11/2014 | Kwon et al. |
| 2014/0335541 A1 | 11/2014 | Kwon et al. |
| 2015/0111232 A1 | 4/2015 | Kwon |
| 2016/0153996 A1 | 6/2016 | Kwon et al. |
| 2016/0154000 A1 | 6/2016 | Kwon |
| 2016/0251437 A1 | 9/2016 | Dong et al. |

(56) References Cited

U.S. PATENT DOCUMENTS

| | | |
|---|---|---|
| 2017/0089918 A1 | 3/2017 | Dong |
| 2017/0173030 A1 | 6/2017 | Dong |
| 2017/0363634 A1 | 12/2017 | Kwon et al. |

FOREIGN PATENT DOCUMENTS

| | | |
|---|---|---|
| WO | WO 1990/07861 | 7/1990 |
| WO | WO 1991/10741 | 7/1991 |
| WO | WO 1991/11465 | 8/1991 |
| WO | WO 1991/17271 | 11/1991 |
| WO | WO 1992/00092 | 1/1992 |
| WO | WO 1992/01047 | 1/1992 |
| WO | WO 1992/20791 | 11/1992 |
| WO | WO 1993/01222 | 1/1993 |
| WO | WO 1995/05464 | 2/1995 |
| WO | WO 1995/07707 | 3/1995 |
| WO | WO 1996/29348 | 9/1996 |
| WO | WO 1997/17613 | 5/1997 |
| WO | WO 1997/17614 | 5/1997 |
| WO | WO 1997/24447 | 7/1997 |
| WO | WO 1998/16249 | 4/1998 |
| WO | WO 1998/23635 | 6/1998 |
| WO | WO 1998/33914 | 8/1998 |
| WO | WO 1998/36096 | 8/1998 |
| WO | WO 1999/36093 | 7/1999 |
| WO | WO 1999/64597 | 12/1999 |
| WO | WO 2000/026342 | 5/2000 |
| WO | WO 2000/029445 | 5/2000 |
| WO | WO 2000/029582 | 5/2000 |
| WO | WO 2000/041508 | 7/2000 |
| WO | WO 2000/055375 | 9/2000 |
| WO | WO 2000/061612 | 10/2000 |
| WO | WO 2001/034629 | 5/2001 |
| WO | WO 2001/062905 | 8/2001 |
| WO | WO 2001/070979 | 9/2001 |
| WO | WO 2001/083750 | 11/2001 |
| WO | WO 2001/094413 | 12/2001 |
| WO | WO 2002/000692 | 1/2002 |
| WO | WO 2002/000730 | 1/2002 |
| WO | WO 2002/002587 | 1/2002 |
| WO | WO 2002/002891 | 1/2002 |
| WO | WO 2002/008279 | 1/2002 |
| WO | WO 2002/078731 | 1/2002 |
| WO | WO 2002/024891 | 3/2002 |
| WO | WO 2002/046449 | 6/2002 |
| WO | WO 2002/057453 | 7/2002 |
| WO | WO 2002/079474 | 10/2002 |
| WO | WO 2002/081731 | 10/2002 |
| WO | WO 2002/086083 | 10/2002 |
| WO | WO 2003/006632 | 1/2003 |
| WO | WO 2003/008583 | 1/2003 |
| WO | WO 2003/049755 | 6/2003 |
| WO | WO 2004/085418 | 10/2004 |
| WO | WO 2006/042237 | 4/2006 |
| WO | WO 2006/050172 | 5/2006 |
| WO | WO 2006/133396 | 12/2006 |
| WO | WO 2008/037080 | 4/2008 |
| WO | WO 2008/083174 | 7/2008 |
| WO | WO 2009/023566 | 2/2009 |
| WO | WO 2009/029342 | 3/2009 |
| WO | WO 2009/114110 | 9/2009 |
| WO | WO 2010/027423 | 3/2010 |
| WO | WO 2010/027827 | 3/2010 |
| WO | WO 2010/027828 | 3/2010 |
| WO | WO 2010/098788 | 9/2010 |
| WO | WO 2011/066342 | 6/2011 |
| WO | WO 2011/066389 | 6/2011 |
| WO | WO 2013/003112 | 2/2013 |
| WO | WO 2013/019906 | 2/2013 |
| WO | WO 2013/090552 | 6/2013 |
| WO | WO 2013/132044 | 9/2013 |
| WO | WO 2015/050663 | 4/2015 |
| WO | WO 2015/179654 | 11/2015 |
| WO | WO 2016/014148 | 1/2016 |

OTHER PUBLICATIONS

Barber et al., "Restoring function in exhausted CD8 T cells during chronic viral infection," *Nature*, 439(7077):682-687, Epub Dec. 28, 2005.

Betts et al., "Sensitive and viable identification of antigen-specific CD8+ T cells by a flow cytometric assay for degranulation," *J Immunol Methods.*, 281(1-2):65-78, Oct. 1, 2003.

Blank et al., "PD-L1/B7H-1 inhibits the effector phase of tumor rejection by T cell receptor (TCR) transgenic CD8+ T cells," *Cancer Res.*, 64(3):1140-1145, Feb. 1, 2004.

Boggio et al., "Interleukin 12-mediated prevention of spontaneous mammary adenocarcinomas in two lines of Her-2/neu transgenic mice," *J Exp Med.*, 188(3):589-596, Aug. 3, 1998.

Brinkmann et al., "FTY720: altered lymphocyte traffic results in allograft protection," *Transplantation.*, 72(5):764-769, Sep. 15, 2001.

Crispe, "Hepatic T cells and liver tolerance," *Nat Rev Immunol.*, 3(1):51-62, Jan. 2003.

Dong and Chen, "B7-H1 pathway and its role in the evasion of tumor immunity," *J Mol Med (Berl).*, 81(5):281-287, Epub Apr. 30, 2003.

Dong et al., "B7-H1 determines accumulation and deletion of intrahepatic CD8(+) T lymphocytes," *Immunity.*, 20(3):327-336, Mar. 2004.

Dong et al., "Tumor-associated B7-H1 promotes T-cell apoptosis: a potential mechanism of immune evasion," *Nat Med.*, 8(8):793-800, Epub Jun. 24, 2002.

Duraiswamy et al., "Replenish the source within: Rescuing tumor-infiltrating lymphocytes by double checkpoint blockade," *Oncoimmunology.*, 2(10):e25912. Epub Aug. 2, 2013.

GenBank® Accession No. AAH74740.1, GI No. 49902307, "Programmed cell death 1 [*Homo sapiens*]," Jul. 15, 2006, 2 pages.

GenBank® Accession No. AAX29153.1, GI No. 60652917, "integrin alpha L, partial [synthetic construct]," Mar. 29, 2005, 2 pages.

GenBank® Accession No. BC008777.2, GI No. 33870544, "Homo sapiens integrin, alpha L (antigen CD11A (p180), lymphocyte function-associated antigen 1; alpha polypeptide), mRNA (cDNA clone MGC:1714 IMAGE:3142951), complete cds," 4 pages.

GenBank® Accession No. BC074740.2, GI No. 50960296, "*Homo sapiens* programmed cell death 1, mRNA (cDNA clone MGC:103817 IMAGE:30915198), complete cds," Jul. 15, 2006, 3 pages.

Gibbons et al., "B7-H1 limits the entry of effector CD8(+) T cells to the memory pool by upregulating Bim," Oncoimmunology, 1(7):1061-1073, Oct. 1, 2012.

Harrington et al., "Differentiating between memory and effector CD8 T cells by altered expression of cell surface O-glycans," *J Exp Med.*, 191(7):1241-1246, Apr. 3, 2000.

Iwai et al., "Involvement of PD-L1 on tumor cells in the escape from host immune system and tumor immunotherapy by PD-L1 blockade," *Proc Natl Acad Sci U S A.*, 99(19):12293-12297, Epub Sep. 6, 2002.

Katou et al., "Differing phenotypes between intraepithelial and stromal lymphocytes in early-stage tongue cancer," *Cancer Res.*, 67(23):11195-11201, Dec. 1, 2007.

Kim et al., "Features of responding T cells in cancer and chronic infection," *Curr Opin Immunol.*, 22(2):223-230, Epub Mar. 6, 2010.

Lazarevic and Glimcher, "T-bet in disease," *Nat Immunol.*, 12(7):597-606, Jun. 20, 2011.

Lewis et al., "Surrogate tumor antigen vaccination induces tumor-specific immunity and the rejection of spontaneous metastases," *Cancer Res.*, 65(7):2938-2946, Apr. 1, 2005.

Lunsford et al., "Targeting LFA-1 and cd154 suppresses the in vivo activation and development of cytolytic (cd4-Independent) CD8+ T cells," *J Immunol.*, 175(12):7855-7866, Dec. 15, 2005.

McDermott et al., "PD-1 as a potential target in cancer therapy," *Cancer Med.*, 2(5):662-673. Epub Jul. 21, 2013.

Mumprecht et al., "Programmed death 1 signaling on chronic myeloid leukemia-specific T cells results in T-cell exhaustion and disease progression," *Blood.*, 114(8):1528-1536. Epub May 6, 2009.

(56) References Cited

OTHER PUBLICATIONS

Nava-Parada et al., "Peptide vaccine given with a Toll-like receptor agonist is effective for the treatment and prevention of spontaneous breast tumors," *Cancer Res.*, 67(3):1326-1334, Feb. 1, 2007.
Rai et al., "Tracking the total CD8 T cell response to infection reveals substantial discordance in magnitude and kinetics between inbred and outbred hosts," *J Immunol.*, 183(12):7672-7681, Dec. 15, 2009.
Schmidt et al "Extreme CD8 T cell requirements for anti-malarial liver-stage immunity following immunization with radiation attenuated sporozoites," *PLoS Pathog.*, 6(7):e1000998, Jul. 15, 2010.
Schmits et al., "LFA-1-deficient mice show normal CTL responses to virus but fail to reject immunogenic tumor," *J Exp Med.*, 183(4):1415-1426, Apr. 1, 1996.
Seki et at., "Tumor-specific CTL kill murine renal cancer cells using both perforin and Fas ligand-mediated lysis in vitro, but cause tumor regression in vivo in the absence of perforin," *J Immunol.*, 168(7):3484-3492, Apr. 1, 2002.
Smith et al., Differential outcome of IL-2/anti-IL-2 complex therapy on effector and memory CD8+ T cells following vaccination with an adenoviral vector encoding EBV epitopes, *J Immunol.*, 186(10):5784-5790, Epub Apr. 11, 2011.
Thompson et al., "PD-1 is expressed by tumor-infiltrating immune cells and is associated with poor outcome for patients with renal cell carcinoma," *Clin Cancer Res.*, 13(6):1757-1761, Mar. 15, 2007.
Thompson et al., "Tumor masses support naive T cell infiltration, activation, and differentiation into effectors," *J Exp Med.*, 207(8):1791-1804, Epub Jul. 26, 2010.
Truneh et al., "Early steps of lymphocyte activation bypassed by synergy between calcium ionophores and phorbol ester," *Nature.*, 313(6000).318-320, Jan. 24-30, 1985.
Vesely et al., "Natural innate and adaptive immunity to cancer," *Annu Rev Immunol.*, 29:235-271, 2011.
Zhang et al., "PD-1/PD-L1 interactions inhibit antitumor immune responses in a murine acute myeloid leukemia model," *Blood*, 114(8):1545-1552, Epub May 5, 2009.
Academic Press Dictionary of Science and Technology (definition for the term "polyclonal"; Oxford: Elsevier Science & Technology (1996); retrieved Oct. 22, 2008, from http://www.credoreference.con/entry/3144515/.
Acsadi et al., "Direct gene transfer and expression into rat heart in vivo," *New Biol.*, 3(1):71-81, Jan. 1991.
Adachi et al., "Enhanced and accelerated lymphoproliferation in Fas-null mice. " *Proc Natl Acad Sci U S A.*, 93(5):2131-2136, Mar. 5, 1996.
Adachi et al., "Aberrant transcription caused by the insertion of an early transposable element in an intron of the Fas antigen gene of lpr mice," *Proc Natl Acad Sci U S A.* 90(5):1756-1760, Mar. 1, 1993.
Agata et al., "Expression of the PD-1 antigen on the surface of stimulated mouse T and B lymphocytes," *Int Immunol.*, 8(5):765-772, May 1996.
Ahonen et al., "Combined TLR and CD40 triggering induces potent CD8+ T cell expansion with variable dependence on type I IFN," *J Exp Med.*, 199(6):775-784, Epub Mar. 8, 2004.
Alderson et al., "Molecular and biological characterization of human 4-1BB and its ligand," *Eur J Immunol.*, 24(9):2219-2227, Sep. 1994.
Aldovini et al., "Humoral and cell-mediated immune responses to live recombinant BCG-HIV vaccines," *Nature*, 351(6326):479-482, Jun. 6, 1991.
Allie et al., "Programmed death 1 regulates development of central memory CD8 T cells after acute viral infection," *J Immunol.*, 186(11):6280-6286, Epub Apr. 27, 2011.
Ambrosini et al., "A novel anti-apoptosis gene, survivin, expressed in cancer and lymphoma," *Nat Med.*, 3(8):917-921, Aug. 1997.
Anderson, "Human gene therapy," *Science*, 256(5058):808-813, May 8, 1992.

Andorsky et al., "Programmed death ligand 1 is expressed by non-hodgkin lymphomas and inhibits the activity of tumor-associated T cells," *Clin Cancer Res.*, 17(13):4232-4244, Epub May 3, 2011.
Ansari et al., "The programmed death-1 (PD-1) pathway regulates autoimmune diabetes in nonobese diabetic (NOD) mice," *J Exp Med.*, 198(1):63-69, Jul. 7, 2003.
Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," *Microbes Infect.*, 8(6):1450-1454, Epub Mar. 29, 2006.
Attwood et al., "Genomics. The Babel of bioinformatics," *Science*, 290(5491):471-473, Oct. 20, 2000.
Azuma et al., "B7-H1 is a ubiquitous antiapoptotic receptor on cancer cells," *Blood.* 111(7):3635-3643, Epub Jan. 25, 2008.
Baitsch et at, "Exhaustion of tumor-specific $CD8^+$ T cells in metastases from melanoma patients," *J Clin Invest.*, 121(6):2350-2360, Epub May 9, 2011.
Bajorath et al., "Molecular modeling of CD28 and three-dimensional analysis of residue conservation in the CD28/CD152 family," *J Mol Graph Model.*, 15(2):135-9, 108-111, Apr. 1997.
Baldrick, "Pharmaceutical excipient development: the need for preclinical guidance " *Regul Toxicol Pharmacol.*, 32(2):210-218, Oct. 2000.
Banáth et al., "Residual gammaH2AX foci as an indication of lethal DNA lesions," *BMC Cancer.*, 10:4, Jan. 5, 2010.
BD PharmingenTM Technical Data Sheet, "Purified Rat Anti-Mouse Ly-6G (Gr-1) Monoclonal Antibody for Immunohistochemistry (IHC)" 1 page, 2003.
Benita et al., "Characterization of drug-loaded poly(d,l-lactide) microspheres," *J Pharm Sci.*, 73(12):1721-1724, Dec. 1984.
Benlalam et al., "Comprehensive analysis of the frequency of recognition of melanoma-associated antigen (MAA) by CD8 melanoma infiltrating lymphocytes (TIL) implications for immunotherapy," *Eur J Immunol.*, 31(7):2007-2015, Jul. 31, 2001.
Bennardo et al., "Alternative-NHEJ is a mechanistically distinct pathway of mammalian chromosome break repair," *PLoS Genet.*, 4(6):e1000110, Jun. 27, 2008.
Berman et al., "The Protein Data Bank," *Nucleic Acids Res.*, 28(1):235-242, Jan. 1, 2000.
Berrien-Elliott et al., "Durable adoptive immunotherapy for leukemia produced by manipulation of multiple regulatory pathways of CD8+ T-cell tolerance," *Cancer Res.*, 73(2):605-616, Jan. 15, 2013.
Berthon et al., "In acute myeloid leukemia, B7-H1 (PD-L1) protection of blasts from cytotoxic T cells is induced by TLR ligands and interferon-gamma and can be reversed using MEK inhibitors," *Cancer Immunol Immunother.*, 59(12):1839-1849, Epub Sep. 4, 2010.
Bird et al., "Single-chain antigen-binding proteins," *Science*, 242(4877):423-426, Oct. 21, 1988.
Blank et al., "Blockade of PD-L1 (B7-H1) augments human tumor-specific T cell responses in vitro," *Int J Cancer*, 119(2):317-327, Jul. 15, 2006.
Blank et al., "Interaction of PD-L1 on tumor cells with PD-1 on tumor-specific T cells as a mechanism of immune evasion: implications for tumor immunotherapy " *Cancer Immunol Immunother.*, 54(4):307-314, Epub Dec. 15, 2004.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells," *J Immunol* , 157(8):3250-3259, Oct. 15, 1996.
Block, "Medicated Applications," Remington's Pharmaceutical Sciences, 18th edition, Mack Publishing Company, Easton, PA, Chpt 87, pp. 1596-1614, 1990.
Bodine, "mTOR signaling and the molecular adaptation to resistance exercise," Med Sci Sports Exerc., 38(11):1950-1957, Nov. 2006.
Boise et al., "CD28 costimulation can promote T cell survival by enhancing the expression of Bcl-XL," *Immunity*, 3(1):87-98, Jul. 1995.

(56) References Cited

OTHER PUBLICATIONS

Boletta et al., "High efficient non-viral gene delivery to the rat kidney by novel polycationic vectors," *J Am Soc Nephrol.*, 7(9):1728, abstr A2409, Sep. 1, 1996.
Bona et al., "Immune response: Idiotype anti-idiotype network," *CRC Crit Rev Immunol.*, 33-81, Mar. 1981.
Bonfoco et al., "Inducible nonlymphoid expression of Fas ligand is responsible for superantigen-induced peripheral deletion of T cells," *Immunity*, 9(5):711-720, Nov. 1998.
Bonifaz et al., "Efficient targeting of protein antigen to the dendritic cell receptor DEC-205 in the steady state leads to antigen presentation on major histocompatibility complex class I products and peripheral CD8+ T cell tolerance," *J Exp Med.*, 196(12):1627-1638, Dec. 16, 2002.
Bonifaz et al., "In vivo targeting of antigens to maturing dendritic cells via the DEC-205 receptor improves T cell vaccination," *J Exp Med.*, 199(6):815-824, Mar. 15, 2004.
Bonni et al., "Cell survival promoted by the Ras-MAPK signaling pathway by transcription-dependent and -independent mechanisms," *Science*, 286(5443):1358-1362, Nov. 12, 1999.
Boon et al., "Human T cell responses against melanoma," *Annu Rev Immunol.*, 24:175-208, 2006.
Borson et al., "Brain-infiltrating cytolytic T lymphocytes specific for Theiler's virus recognize H2Db molecules complexed with a viral VP2 peptide lacking a consensus anchor residue," *J Virol.*, 71(7):5244-5250, Jul. 1997.
Bouillet and O'Reilly, "CD95, BIM and T cell homeostasis," *Nat Rev Immunol.*, 9(7):514-519, Jul. 2009.
Bowie et al, "Deciphering the message in protein sequences: tolerance to amino acid substitutions," *Science*, 247(4948):1306-1310, Mar. 16, 1990.
Brahmer et al., "Safety and activity of anti-PD-L1 antibody in patients with advanced cancer," *N Engl J Med.*, 366(26):2455-2465, Epub Jun. 2, 2012.
Braquet et al., "Effect of endothelin-1 on blood pressure and bronchopulmonary system of the guinea pig," *J Cardiovasc Pharmacol.*, 13 Suppl 5:S143-6; discussion S150, 1989.
Britton et al., "Leprosy," *Lancet*, 363(9416):1209-1219, Apr. 10, 2004.
Brooks, "Translational genomics: the challenge of developing cancer biomarkers," *Genome Res.*, 22(2):183-187, Feb. 2012.
Brown et al., "Blockade of programmed death-1 ligands on dendritic cells enhances T cell activation and cytokine production," *J Immunol.*, 170(3):1257-1266, Feb. 1, 2003.
Brozovic et al., "Activation of mitogen-activated protein kinases by cisplatin and their role in cisplatin-resistance," *Cancer Lett.*, 251(1):1-16. Epub Nov. 27, 2006.
Bubenik, "Genetically engineered dendritic cell-based cancer vaccines (Review)," *Int J Oncol.*, 18(3):475-478, Mar. 2001.
Burmer et al, "Frequency and spectrum of c-Ki-ras mutations in human sporadic colon carcinoma, carcinomas arising in ulcerative colitis, and pancreatic adenocarcinoma," *Environ Health Perspect.*, 93:27-31, Jun. 1991.
Buskens et al, "Adenocarcinomas of the gastro-esophageal junction: A comparative study of the gastric cardia and the esophagus with respect to cyclooxygenase-2 expression," Digestive Disease Week Abstracts and Itinerary Planner, 2003, abstract No. 850.
Butte et al., "Interaction of human PD-L1 and B7-1," *Mol Immunol.*, 45(13):3567-3572, Epub Jun. 27, 2008.
Butte et al., "PD-L1 interacts specifically with B7-1 to inhibit T cell proliferation," *Immunity.*, 27:111-122, 2007.
Cairns et al., "Immortalization of multipotent growth-factor dependent hemopoietic progenitors from mice transgenic for GATA-1 driven SV40 tsA58 gene," *EMBO J.*, 13(19):4577-4586, Oct. 3, 1994.
Cannons et al., "4-1BB ligand induces cell division, sustains survival, and enhances effector function of CD4 and CD8 T cells with similar efficacy," *J Immunol.*, 167(3):1313-1324, Aug. 1, 2001.

Cao et al., "B7-H1 overexpression regulates epithelial-mesenchymal transition and accelerates carcinogenesis in skin," *Cancer Res.*, 71(4):1235-1243, Epub Dec. 15, 2010.
Carreno et al., "The B7 family of ligands and its receptors: new pathways for costimulation and inhibition of immune responses," *Annu Rev Immunol.*, 20:29-53, Epub Oct. 4, 2001.
Carter et al., "PD-1:PD-L inhibitory pathway affects both CD4(+) and CD8(+) T cells and is overcome by IL-2," *Eur J Immunol.*, 32(3):634-643, Mar. 2002.
Carter et al., "Humanization of an anti-p185HER2 antibody for human cancer therapy " *Proc Natl Acad Sci U S A.*, 89(10):4285-4289, May 15, 1992.
Chakrabarti et al., "Vaccinia virus expression vector: coexpression of beta-galactosidase provides visual screening of recombinant virus plaques," *Mol Cell Biol.*, 5(12):3403-3409, Dec. 1985.
Chambers et al., "Co-stimulation in T cell responses," *Curr Opin Immunol.*, 9(3):396-404, Jun. 1997.
Chan et al., "Autophosphorylation of the DNA-dependent protein kinase catalytic subunit is required for rejoining of DNA double-strand breaks," *Genes Dev.*, 16(18):2333-2338, Sep. 15, 2002.
Chapoval et al., "B7-H3: A costimulatory molecule for T cell activation and IFN-y production," *Nat Immunol.*, 2(3):269-274, Mar. 2001.
Charman, "Lipids, lipophilic drugs, and oral drug delivery-some emerging concepts," *J. Pharm. Sci.*, 89(8):967-978, Aug. 2000.
Chaurand et al., "Peptide and Protein Identification by Matrix-Assisted Laser Desorption Ionization (MALDI) and MALDI-Post-Source Decay Time-of-Flight Mass Spectrometry " *J Am Soc Mass Spectrom.*, 10(2):91-103, Feb. 1999.
Chen et al., "CD44-deficient mice exhibit enhanced hepatitis after concanavalin A injection: evidence for involvement of CD44 in activation-induced cell death," *J Immunol.*, 166(10):5889-5897, May 1, 2001.
Chen et al., "Costimulation of antitumor immunity by the B7 counterreceptor of the T lymphocyte molecules CD28 and CTLA-4," *Cell*, 71(7):1093-1102, Dec. 24, 1992.
Chen et al., "Tumor immunogenicity determines the effect of co-stimulation by B7 on T-cell mediated tumor immunity," *J Exp Med.* 179(2):523-532, Feb. 1, 1994.
Chen, "Co-inhibitory molecules of the B7-CD28 family in the control of T-cell immunity " *Nat Rev Immunol.*, 4(5):336-347, May 2004.
Cheville et al., "Comparisons of outcome and prognostic features among histologic subtypes of renal cell carcinoma," *Am J Surg Pathol.*, 27(5):612-624, May 2003.
Choi et al., "Genomic Organization and expression Analysis of B7-H4, an Immune Inhibitory Molecule of the B7 Family," *J Immunol.*, 171(9):4650-4654, Nov. 1, 2003.
Cogoni et al. "Transgene silencing of the al-1 gene in vegetative cells of Neurospora is mediated by a cytoplasmic effector and does not depend on DNA-DNA interactions or DNA methylation ," *EMBO J.*, 15(12):3153-3163, Jun. 17, 1996.
Cogoni et al., "Gene silencing in Neurospora crassa requires a protein homologous to RNA-dependent RNA polymerase," *Nature*, 399(6732):166-169, May 13, 1999.
Cohen et al., "Lpr and gld: Single Gene Models of Systemic Autoimmunity and Lymphoproliferative Disease," *Annu Rev Immunol.*, 9:243-269, 1991.
Cole et al., "The EBV-hybridoma technique and its application to human lung cancer," *Monoclonal Antibodies and Cancer Therapy*, 27:77-96, Jan.-Feb. 1985.
Collins et al., "The B7 family of immune-regulatory ligands," *Genome Biol.*, 6(6):223, 7 pages, Epub May 31, 2005.
Collis et al., "The life and death of DNA-PK," *Oncogene.*, 24(6):949-961, Feb. 3, 2005.
Conacci-Sorrell et al., "Autoregulation of E-cadherin expression by cadherin-cadherin interactions: the roles of beta-catenin signaling, Slug, and MAPK," *J Cell Biol.*, 163(4):847-857, Epub Nov. 17, 2003.
Cone et al., "High-efficiency gene transfer into mammalian cells: generation of helper-free recombinant retrovirus with broad mammalian host range," *Proc Natl Acad Sci U S A.*, 81(20):6349-6353, Oct. 1984.

(56) References Cited

OTHER PUBLICATIONS

Connolly, "Analytical molecular surface calculation," *J Appl Crystallogr.*, 16(5):548-558, Oct. 1, 1983.
Corpet, "Multiple sequence alignment with hierarchical clustering," *Nucleic Acids Res.*, 16(22):10881-10890, Nov. 25, 1988.
Cote et al., "Generation of human monoclonal antibodies reactive with cellular antigens," *Proc Natl Acad Sci U S A.*, 80(7):2026-2030, Apr. 1983.
Coyle et al., "The expanding B7 superfamily: increasing complexity in costimulatory signals regulating T cell function," *Nat Immunol.*, 2(3):203-209, Mar. 2001.
Crispe et al., "The liver as a site of T-cell apoptosis: graveyard, or killing field?" *Immunol Rev.*, 174:47-62, Apr. 2000.
Cristiano et al., "Molecular conjugates: a targeted gene delivery vector for molecular medicine," *J Mol Med (Berl).*, 73(10):479-486, Oct. 1995.
Crystal, "Gene therapy strategies for pulmonary disease" *Am J Med.*, 92(suppl 6A):44S-52S, Jun. 22, 1992.
Curiel et al., "Blockade of B7-H1 improves myeloid dendritic cell-mediated antitumor immunity," *Nat Med.*, 9(5):562-567, Epub Apr. 21, 2003.
Dao et al., "Involvement of CD1 in peripheral deletion of T lymphocytes is independent of NK T cells," *J Immunol.*, 166(5):3090-3097, Mar. 1, 2001.
Database EM-MUS [Online]EMBL; Accession No. AF142780.1 (version 1), Jun. 1, 1999, 2 pages.
Datta et al., "Akt phosphorylation of BAD couples survival signals to the cell-intrinsic death machinery," *Cell.*, 91(2):231-241, Oct. 17, 1997.
Davidson et al., "Phenotypic, functional, and molecular genetic comparisons of the abnormal lymphoid cells of C3H-lpr/lpr and C3H-gld/gld mice," *J Immunol.*, 136(11):4075-4084, Jun. 1, 1986.
Davidson et al., "Small Molecules, Inhibitors of DNA-PK, Targeting DNA Repair, and Beyond," *Front Pharmacol.*, vol. 4, Article 5, pp. 1-7, Jan. 31, 2013.
de StGroth et al., "Production of monoclonal antibodies: strategy and tactics," *J Immunol Methods.*, 35(1-2):1-21, 1980.
Debs et al., "Lung-specific delivery of cytokines induces sustained pulmonary and systemic immunomodulation in rats," *J Immunol.*, 140(10):3482-3488, May 15, 1988.
del Peso et al., "Interleukin-3-induced phosphorylation of BAD through the protein kinase Akt," *Science*, 278(5338):687-689, Oct. 24, 1997.
Dheda et al., "Lung remodeling in tuberculosis," *J Infect Dis.*, 192(7):1201-1209, Epub Aug. 29, 2005.
Diehl et al., "In vivo triggering through 4-1BB enables Th-independent priming of CTL in the presence of an intact CD28 costimulatory pathway," *J Immunol.*, 168(8):3755-3762, Apr. 15, 2002.
Ding et al., "Release of reactive nitrogen intermediates and reactive oxygen intermediates from mouse peritoneal macrophages. Comparison of activating cytokines and evidence for independent production," *J Immunol.*, 141(7):2407-2412, Oct. 1, 1988.
Dini, "Recognizing death: liver phagocytosis of apoptotic cells," *Eur J Histochem.*, 44(3):217-227, 2000.
Doering et al., "Network analysis reveals centrally connected genes and pathways involved in CD8+ T cell exhaustion versus memory," *Immunity*, 37(6):1130-1144, Epub Nov. 15, 2012.
Dong et al., "B7-H1, a third member of the B7 family, co-stimulates T-cell proliferation and interleukin-10 secretion," Nat Med., 5(12):1365-1369, Dec. 1999.
Dong et al., "Immune regulation by novel costimulatory molecules," *Immunol Res.*, 28(1):39-48, 2003.
Dong et al., "Immunoregulatory role of B7-H1 in chronicity of inflammatory responses," *Cell Mol Immunol.*, 3(3):179-187, Jun. 2006.
Dragoi et al., "DNA-PKcs, but not TLR9, is required for activation of Akt by CpG-DNA," *EMBO J.*, 24(4):779-789, Epub Jan. 27, 2005.
Dronca et al., "Soluble PD-L1 (sPD-L1) is associated with decreased survival in metastatic melanoma," Society for Melanoma Research 2015 Congress, San Francisco, CA, Nov. 18-21, 2015 [abstract].
Dudler et al., "Gene transfer of programmed death Ligand-1.Ig prolongs cardiac allograft survival," *Transplantation*, 82(12):1733-1737, Dec. 27, 2006.
Dunussi-Joannopoulos et al., "Gene therapy with B7.1 and GM-CSF vaccines in a murine AML model," *J Pediatr Hematol Oncol.*, 19(6):536-540, Nov.-Dec. 1997.
Ehl et al., "Different susceptibility of cytotoxic T cells to CD95 (Fas/Apo-1) ligand-mediated cell death after activation in vitro versus in vivo," *J Immunol.*, 156(7):2357-2360, Apr. 1, 1996.
Elliott et al., "Mitoxantrone in combination with an inhibitor of DNA-dependent protein kinase: a potential therapy for high risk B-cell chronic lymphocytic leukaemia," *Br J Haematol.*, 152(1):61-71, Epub Nov. 18, 2010.
EMBL-EBI Accession No. AF 142780.2 "Mus musculus butyrophilin-like protein (Btdc) mRNA, complete cds," created Jun. 1, 1999, 2 pages.
EMBL-EBI Accession No. Q9WUL5, "Programmed cell death 1 ligand 2," Nov. 1, 1999, 5 pages.
Engh et al., "Accurate bond and angle parameters for X-ray protein structure refinement," *Acta Cryst.*, A47(4):392-400, Jul. 1, 1991.
Falkner et al., "pUV I: a new vaccinia virus insertion and expression vector," *Nucleic Acids Res.*, 15(17):7192, Sep. 11, 1987.
Farley et al., "p38 mitogen-activated protein kinase mediates the Fas-induced mitochondrial death pathway in CD8+ T cells," *Mol Cell Biol.*, 26(6):2118-2129, Mar. 2006.
Fechteler et al., "Prediction of protein three-dimensional structures in insertion and deletion regions: a procedure for searching data bases of representative protein fragments using geometric scoring criteria," *J Mol Biol.*, 253(1):114-131, Oct. 13, 1995.
Feng et al., "Identification of a PKB/Akt hydrophobic motif Ser-473 kinase as DNA-dependent protein kinase," *J Biol Chem.*, 279(39):41189-41196, Epub Jul. 15, 2004.
Figlin et al., "Treatment of metastatic renal cell carcinoma with nephrectomy, interleukin-2 and cytokine-primed or CD8(+) selected tumor infiltrating lymphocytes from primary tumor," *J Urol.*, 158(3 Pt 1):740-745, Sep. 1997.
Finck et al., "Treatment of Murine Lupus with CTLA41g," *Science*, 265(5176):1225-1227, Aug. 26, 1994.
Fire et al., "Potent and specific genetic interference by double-stranded RNA in Caenorhabditis elegans," *Nature*, 391(6669):806-811, Feb. 19, 1998.
Fleming et al., Selective expression of Ly-6G on myeloid lineage cells in mouse bone marrow. RB6-8C5 mAb to granulocyte-differentiation antigen (Gr-1) detects members of the Ly-6 family, *J Immunol.*, 151(5):2399-2408, Sep. 1, 1993.
Foell et al., "CD137 costimulatory T cell receptor engagement reverses acute disease in lupus-prone NZB x NZW F1 mice," *J Clin Invest.*, 111(10):1505-1518, May 2003.
Foell et al., "CD137-Mediated T Cell Co-Stimulation Terminates Existing Autoimmune Disease in SLE-Prone NZB/NZW F1 Mice," *Ann N Y Acad Sci.*, 987:230-235, Apr. 2003.
Fortugno et al., "Survivin exists in immunochemically distinct subcellular pools and is involved in spindle microtubule function," *J Cell Sci.*, 115(Pt 3):575-585, Feb. 1, 2002.
Frank et al., "An outcome prediction model for patients with clear cell renal cell carcinoma treated with radical nephrectomy based on tumor stage, size, grade and necrosis: the SSIGN score," *J Urol.*, 168(6):2395-2400, Dec. 2002.
Freeman et al., "B7, a new member of the Ig superfamily with unique expression on activated and neoplastic B cells," *J Immunol.*, 143(8):2714-2722, Oct. 15, 1989.
Freeman et al., "Cloning of B7-2: a CTLA-4 counter-receptor that co stimulates human T cell proliferation," *Science*, 262(5135):909-911, Nov. 5, 1993.
Freeman et al., "Engagement of the PD-1 ImmunoInhibitory receptor by a novel B7 family member leads to negative regulation of lymphocyte activation," *J Exp Med.*, 192(7):1027-1034, Oct. 2, 2000.

(56) References Cited

OTHER PUBLICATIONS

Freeman et al., "Structure, expression, and T cell proliferation costimulatory activity of the murine homologue of the human B lymphocyte activation antigen B7," *J Exp Med.*, 174(3):625-631, Sep. 1, 1991.
Friedmann et al., "Interaction of the epidermal growth factor receptor and the DNA-dependent protein kinase pathway following gefitinib treatment," *Mol Cancer Ther.*, 5(2):209-218, Feb. 2006.
Frigola et al., "Identification of a soluble form of B7-H1 that retains immunosuppressive activity and is associated with aggressive renal cell carcinoma," *Clin Cancer Res.*, 17(7):1915-1923, Apr. 1, 2011.
Fuerst et al., "Transfer of the inducible lac repressor/operator system from *Escherichia coli* to a vaccinia expression vector," *Proc Natl Acad Sci U S A.*, 86(8):2549-2553, Apr. 1989.
Fyfe et al., "Results of treatment of 255 patients with metastatic renal cell carcinoma who received high-dose recombinant interleukin-2 therapy," *J Clin Oncol.*, 13(3):688-696, Mar. 1995.
GenBank Accession No. AAC51660 "apoptosis inhibitor survivin [*Homo sapiens*]," Sep. 2, 2004, 2 pages.
GenBank Accession No. AAP37283, "immune costimulatory protein B7-H4 [*Homo sapiens*]," Jun. 1, 2003, 1 page.
GenBank Accession No. AK001872.1,"*Homo sapiens* cDNA FLJ11010 fis, clone PLACE1003145," Feb. 22, 2000, 2 pages.
GenBank Accession No. AL162253, "Human DNA sequence from clone RP11-574F11 on chromosome 9 contains the gene for B7-H1 protein (PD-L1), the gene for programmed death ligand 2 (PDL2) (PDCD1L2) and a novel gene, complete sequence" Feb. 24, 2008, 35 pages.
GenBank Accession No. AY280972, "*Homo sapiens* immune costimulatory protein B7-H4 mRNA, complete cds," Jun. 1, 2003, 1 page.
GenBank Accession No. NM_005191.3 (GI No. 113722122), "*Homo sapiens* CD80 molecule (CD80), mRNA," Jun. 15, 2013, 5 pages.
GenBank Accession No. NP_005182.1 (GI No. 4885123), "T-lymphocyte activation antigen CD80 precursor [*Homo sapiens*]," Jun. 15, 2013, 3 pages.
GenBank Accession No. U75285 "*Homo sapiens* apoptosis inhibitor survivin gene, complete cds," Sep. 2, 2004, 5 pages.
GenBank® Accession No. AAF25807 (GI No. 6708119), "B7-H1 [*Homo sapiens*]," Jan. 18, 2000, 2 pages.
GenBank® Accession No. AF177937 (GI No. 6708118), "*Homo sapiens* B7-H1 mRNA, complete cds," Jan. 18, 2000, 1 page.
GenBank® Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 IMAGE:3142951), complete cds," Jul. 28, 2005, 4 pages.
Gerdes et al. "Cell cycle analysis of a cell proliferation-associated human nuclear antigen defined by the monoclonal antibody Ki-67," *J Immunol.*, 133(4):1710-1715, Oct. 1984.
Gerstmayer et al., "Costimulation of T cell proliferation by a chimeric B7-2 antibody fusion protein specifically targeted to cells expressing the erbB2 proto-oncogene," *J Immunol.*, 158(10):4584-4590, May 15, 1997.
Gerstmayer et al., "Costimulation of T-cell proliferation by a chimeric B7 antibody fusion protein," *Cancer Immunol Immunother.*, 45(3-4):156-158, Nov.-Dec. 1997.
Gevaert et al., "Protein identification based on matrix assisted laser desorption/ionization-post source decay-mass spectrometry," *Electrophoresis*, 22(9):1645-1651, May 2001.
Ghebeh et al., "Doxorubicin downregulates cell surface B7-H1 expression and upregulates its nuclear expression in breast cancer cells: role of B7-H1 as an anti-apoptotic molecule, " *Breast Cancer Res.*, 12(4):R48, Epub Jul. 13, 2010.
Ghebeh et al., "The B7-H1 (PD-L1) T lymphocyte-inhibitory molecule is expressed in breast cancer patients with infiltrating ductal carcinoma: correlation with important high risk prognostic factors," *Neoplasia*, 8(3):190-198, Mar. 2006.
Gillings et al., "Apoptosis and autophagy: BIM as a mediator of tumour cell death in response to oncogene-targeted therapeutics," *FEBS J.*, 276(21):6050-6062, Epub Sep. 29, 2009.
Gimmi et al., "B-cell surface antigen B7 provides a costimulatoly signal that induces T cells to proliferate and secrete interleukin 2," *Proc Natl Acad Sci U S A.*, 88(9):3671-3675, May 1, 1991.
Goodwin et al., "Molecular cloning and expression of the type 1 and type 2 murine receptors for tumor necrosis factor," *Mol Cell Biol.*, 11(6):3020-3026, Jun. 1991.
Goodwin et al., "Molecular cloning of a ligand for the inducible T cell gene 4-1BB: a member of an emerging family of cytokines with homology to tumor necrosis factor," *Eur J Immunol.*, 23(10):2631-2641, Oct. 1993.
Green et al., "Activation-induced cell death in T cells," *Immunol Rev.*, 193:70-81, Jun. 2003.
Green et al., "Antigen-specific human monoclonal antibodies from mice engineered with human Ig heavy and light chain YACs," *Nat Genet.*, 7(1):13-21, May 1994.
Greenwald et al., "The B7 family revisited," *Annu Rev Immunol.*, 23:515-548, 2005.
Grivennikov et al. "Immunity, inflammation, and cancer," *Cell.*, 140(6):883-899, Mar. 19, 2010.
Guatelli et al., "Isothermal, in vitro amplification of nucleic acids by a multi enzyme reaction modeled after retroviral replication," *Proc Natl Acad Sci U S A.*, 87(5):1874-1878, Mar. 1990.
Guinn et al., "4-1BBL cooperates with B7-1 and B7-2 in converting a B cell lymphoma cell line into a long-lasting antitumor vaccine," *J Immunol.*, 162(8):5003-5010, Apr. 15, 1999.
Guam et al., "Correct end use during end joining of multiple chromosomal double strand breaks is influenced by repair protein RAD50, DNA-dependent protein kinase DNA-PKcs, and transcription context," *J Biol Chem.*, 286(49):42470-42482, Epub Oct. 24, 2011.
Guo et al., "A novel fusion protein of IP1 O-scFv retains antibody specificity and chemokine function," *Biochem Biophys Res Commun.*, 320(2):506-513, Jul. 23, 2004.
Haendeler et al., "Nitric Oxide and Apoptosis," *Vitam Horm.*, 57:49-77, 1999.
Hansen et al., "Monoclonal antibodies identifying a novel T-cell antigen and Ia antigens of human lymphocytes," *Immunogenetics*, 10(1-4):247-260, Feb. 1, 1980.
Harlow and Lane., "Antibodies: A Laboratory Manual," Cold Spring Harbor Laboratory Press, Cold Spring Harbor, NY, pp. 553, 555-582, 584-589, 591-612, 1988.
Hatzoglou et al., "Hepatic gene transfer in animals using retroviruses containing the promoter from the gene for phosphoenolpyruvate carboxykinase" *J Biol Chem.*, 265(28):17285-17293, Oct. 5, 1990.
Haugland et al, "Unit 16.5 antibody conjugates for cell biology," *Current Protocosl in cell biology.*, 6:16.5:16.5-16.5.22, Epub May 1, 2001.
Hawiger et al., "Dendritic cells induce peripheral T cell unresponsiveness under steady state conditions in vivo," *J Exp Med.*, 194(6):769-779, Sep. 17, 2001.
Hayakawa et al., "Inhibition of BAD phosphorylation either at serine 112 via extracellular signal-regulated protein kinase cascade or at serine 136 via Akt cascade sensitizes human ovarian cancer cells to cisplatin," *Cancer Res.*, 60(21):5988-5994, Nov. 1, 2000.
He et al., "Identification of a novel splice variant of human PD-L1 mRNA encoding an isoform-lacking Igv-like domain," *Acta Pharmacol Sin.*, 26(4):462-468, Apr. 2005.
Hellstrom et al., "T cell immunity to tumor antigens," *Crit Rev Immunol.*, 18(1-2):1-6, 1998.
Henry et al., "Cloning, structural analysis, and mapping of the B30 and B7 multigenic families to the major histocompatibility complex (MHC) and other chromosomal regions," *Immunogenetics.*, 46(5):383-395, 1997.
Henry et al., "Structure and evolution of the extended B7 family," *Immunol Today*, 20(6):285-288, Jun. 1999.
Hentikoff, "Amino acid substitution matrices from protein blocks," *Proc Natl Acad Sci U S A.*, 89(22):10915-10919, Nov. 15, 1992.
Hestdal et al., "Characterization and regulation of RB6-8C5 antigen expression on murine bone marrow cells," *J Immunol.*, 147(1):22-28, Jul. 1, 1991.
Hildeman et al., "Activated T cell death in vivo mediated by proapoptotic bcl-2 family member bim," *Immunity*, 16(6):759-767, Jun. 2002.

(56) References Cited

OTHER PUBLICATIONS

Hirano et al., "Blockade of B7-H1 and PD-1 by monoclonal antibodies potentiates cancer therapeutic immunity," Cancer Res., 65(3):1089-1096, Feb. 1, 2005.
Hiroishi et al., "Interferon-alpha gene therapy in combination with CDS0 transduction reduces tumorigenicity and growth of established tumor in poorly immunogenic tumor models," Gene Ther., 6(12):1988-1994, Dec. 1999.
Hochman et al., "An active antibody fragment (Fv) composed of the variable portions of heavy and light chains," Biochemistry, 12(6):1130-1135, Mar. 13, 1973.
Hock et al., "Retrovirus-mediated transfer and expression of drug resistance genes in human haematopoietic progenitor cells," Nature, 320:275-277, 1986.
Hoffman, "T Cells in the Pathogenesis of Systemic Lupus Erythematosus," Front Biosci., 6:D1369-D1378, Oct. 1, 2001.
Hoiseth et al., "Aromatic-dependent Salmonella typhimurium are non-virulent and effective as live vaccines," Nature, 291(5812):238-239, May 21, 1981.
Hollinger et al., "Diabodies: small bivalent and bispecific antibody fragments" Proc Natl Acad Sci U S A., 90(14):6444-6448, Jul. 15, 1993.
Holt et al., "Domain antibodies: proteins for therapy," Trends Biotechnol., 21(11):484-490, Nov. 2003.
Hori et al., "B7-H1-induced apoptosis as a mechanism of immune privilege of corneal allografts," J Immunol., 177(9):5928-5935, Nov. 1, 2006.
Huai et al., "Inducible gene expression with the Tet-on system in CD4+ T cells and thymocytes of mice," Genesis, 45(7):427-431, Jul. 2007.
Huang et al., "The liver eliminates T cells undergoing antigen-triggered apoptosis in vivo," Immunity, 1(9):741-749, Dec. 31, 1994.
Huang, "Structural chemistry and therapeutic intervention of protein-protein interactions in immune response, human immunodeficiency virus entry, and apoptosis," Pharmacol Ther., 86(3):201-215, Jun. 2000.
Hubbard et al., "Anti-neutrophil-elastase defenses of the lower respiratory tract in alpha 1-antitrypsin deficiency directly augmented with an aerosol of alpha I-antitrypsin," Ann Intern Med., 111(3):206-212, Aug. 1, 1989.
Hunter, "Diabetes in pregnancy," Effective Care in Pregnancy and Childbirth, Chalmers et al. (eds.), Oxford University Press, vol. 1, pp. 578-593, 1989.
Huse et al., "Generation of a large combinatorial library of the immunoglobulin repertoire in phage lambda," Science, 246(4935):1275-1281, Dec. 8, 1989.
Huston et al., "Protein engineering of antibody binding sites: recovery of specific activity in an anti-digoxin single-chain Fv analogue produced in Escherichia coli," Proc Natl Acad Sci U S A., 85(16):5879-5883, Aug. 1988.
Hutloff et al., "ICOS is an inducible T-cell co-stimulator structurally and functionally related to CD28," Nature 397(6716):263-266, Jan. 21, 1999.
Hyrup et al., "Peptide nucleic acids (PNA): synthesis, properties and potential applications" Bioorg Med Chem., 4(1):5-23, Jan. 31, 1996.
Ichikawa and Chen, "Role of B7-H1 and B7-H4 molecules in down-regulating effector phase of T-cell immunity: novel cancer escaping mechanisms," Front Biosci., 10:2856-2860, Sep. 1, 2005.
Ikemizu et al., "Structure and dimerization of a soluble form of B7-1," Immunity, 12(1):51-60, Jan. 2000.
Ikonomidis, "Delivery of a viral antigen to the class I processing and presentation pathway by Listeria monocytogenes," J Exp Med., 180(6):2209-2218, Dec. 1, 1994.
Inman et al. "PD-L1 (B7-H1) expression by urothelial carcinoma of the bladder and BCG-induced granulomata: associations with localized stage progression," Cancer, 109(8):1499-1505, Apr. 15, 2007.
Inman et al., "Questionable relevance of gamma delta T lymphocytes in renal cell carcinoma," J Immunol., 180(5):3578-3584, Mar. 1, 2008.
Ishida et al., "Differential expression of PD-L1 and PD-L2, ligands for an inhibitory receptor PD-1, in the cells of lymphohematopoietic tissues," Immunol Lett., 84(1):57-62, Oct. 21, 2002.
Ishida et al., "Induced expression of PD-1, a novel member of the immunoglobulin gene superfamily, upon programmed cell death," EMBO J., 11(11):3887-3895, Nov. 1992.
Iwai et al., "PD-1 inhibits antiviral immunity at the effector phase in the liver " J Exp Med., 198(1):39-50, Jul. 7, 2003.
Jacinto et al., "SIN1/MIP1 maintains rictor-mTOR complex integrity and regulates Akt phosphorylation and substrate specificity," Cell, 127(1):125-137, Epub. Sep. 7, 2006.
Jacobson et al., "Unique site of IgG2a and rheumatoid factor production in MRL/lpr mice," Immunol Rev., 156:103-110, Apr. 1997.
Janeway et al. "Immunobiology: the Immune System in Health and Disease," Elsevier Science., 4:36, 1999.
Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosaniine (H2-CMX-Ros) and MitoTracker Red 580 (MTR580)," J Immunol Methods., 306(1-2):68-79, Epub Sep. 29, 2005.
Jeannin et al., "Soluble CD86 is a costimulatoly molecule for human T lymphocytes," Immunity., 13(3):303-312, Sep. 2000.
Jemal et al., "Cancer Statistics, 2005," CA Cancer J Clin, 55(1):10-30, Jan.-Feb. 2005.
Jerne, "Towards a network theory of the immune system," Ann Immunol (Paris). 125C(1-2):373-389, Jan. 1974.
Jiang et al., "Genome-wide association study for biomarker identification of Rapamycin and Everolimus using a lymphoblastoid cell line system," Front Genet., 4:166, Aug. 30, 2013.
Johnston et al., "Biolistic transformation of animal tissue," In Vitro Cell Dev Biol Anim., 27P: 11-14 (1991).
Jones et at, "Replacing the complementarity-determining regions in a human antibody with those from a mouse," Nature, 321(6069):522-525, May 29-Jun. 4, 1986.
Kabat et al., Sequences of Proteins of Immunological Interest, Fifth Edition, U.S. Department of Health and Human Services, NIH Publication No. 91-3242, Table of Contents, 20 pages, 1991.
Kaleko et al., "Persistent gene expression after retrov ral gene transfer into liver cells in vivo," Hum Gene Ther., 2(1).27-32, Spring 1991.
Kaliyaperumal et al., "Antigen-specific therapy of murine lupus nephritis using nucleosomal peptides: tolerance spreading impairs pathogenic function of autoimmune T and B cells," J Immunol., 162(10):5775-5783, May 15, 1999.
Kalled et al., "Anti-CD40 ligand antibody treatment of SNF1 mice with established nephritis: preservation of kidney function," J Immunol., 160(5):2158-2165, Mar. 1, 1998.
Kanas et al., "Blockade of B7-H1 suppresses the development of chronic intestinal inflammation," J Immunol., 171(8):4156-4163, Oct. 15, 2003.
Kaneko et al., "Augmentation of Va14 NKT cell-mediated cytotoxicity by interleukin 4 in an autocrine mechanism resulting in the development of concanavalin A-induced hepatitis " J Exp Med., 191(1):105-114, Jan. 3, 2000.
Karakhanova et al., "ERK/p38 MAP-kinases and PI3K are involved in the differential regulation of B7-H1 expression in DC subsets," Eur J Immunol., 40(1):254-266, Jan. 2010.
Kataoka et al., "Flow cytometric analysis of phosphotylated histone H2AX following exposure to ionizing radiation in human microvascular endothelial cells," J Radiat Res., 47(3-4):245-257, Epub Sep. 2006.
Kaufman et al., "A phase I trial of intra lesional RV-B7.1 vaccine in the treatment of malignant melanoma," Hum Gene Ther., 11(7):1065-1082, May 1, 2000.
Kawabe et al., "Programmed cell death and extrathymic reduction of Vβ8+ CD4+ T cells in mice tolerant to Staphylococcus aureus enterotoxin B," Nature, 349(6306):245-248, Jan. 17, 1991.
Keir et al., "PD-1 and its ligands in tolerance and immunity," Annu Rev Immunol., 26:677-704, 2008.

(56) References Cited

OTHER PUBLICATIONS

Kelley et al., "Cytokines in the Pathogenesis of Systemic Lupus Erythematosus," *Semin Nephrol.*, 19(1):57-66, Jan. 1999.
Kennerdell et al., "Use of dsRNA-mediated genetic interference to demonstrate that frizzled and frizzled 2 act in the wingless pathway," *Cell*, 95(7):1017-1026, Dec. 23, 1998.
Kharbanda et al., "Translocation of SAPK/JNK to mitochondria and interaction with Bcl-x(L) in response to DNA damage," *J Biol Chem.*, 275(1):322-327, Jan. 7, 2000.
Kiessling et al., "High-throughput mutation profiling of CTCL samples reveals KRAS and NRAS mutations sensitizing tumors toward inhibition of the RAS/RAF/MEK signaling cascade " *Blood*, 117(8):2433-2440, Epub Jan. 5, 2011.
Kim et al., "Therapeutic potential of 4-1BB (CD137) as a regulator for effector CD8(+) T cells," *J Hematother Stem Cell Res.*, 10(4):441-449, Aug. 2001.
Köhler et al., "Continuous cultures of fused cells secreting antibody of predefined specificity," *Nature*, 256(5517):495-497, Aug. 7, 1975.
Kohn et al. "Gene therapy for genetic diseases," *Cancer Invest.*, 7(2):179-192, 1989.
Konieczny et al., "The combination of IgM subunits and proteolytic IgG fragment by controlled formation of interchain disulphides," *Haematologia (Budap).*, 14(1):95-99, 1981.
Korkola et al, "Gene expression-based classification of nonseminomatous male germ cell tumors," *Oncogene*, 24(32):5101-5107, Jul. 28, 2005.
Kosari et al, "Clear cell renal cell carcinoma: gene expression analyses identify a potential signature for tumor aggressiveness," *Clin Cancer Res.*, 11(14):5128-5139, Jul. 15, 2005.
Kozbor et al. "The production of monoclonal antibodies from human lymphocytes " *Immunology Today*, 4(3):72-79, Mar. 1, 1983.
Krempski et al., "Tumor-infiltrating programmed death receptor-1+ dendritic cells mediate immune suppression in ovarian cancer," *J Immunol.*, 186(12):6905-6913, Epub May 6, 2011.
Kruege et al., "The role of CD95 in the regulation of peripheral T-cell apoptosis," *Immunol Rev.*, 193:58-69, Jun. 2003.
Krummel et al., "CTLA-4 engagement inhibits IL-2 accumulation and cell cycle progression upon activation of resting T cells," *J Exp Med.*, 183(6):2533-2540, Jun. 1, 1996.
Kuiper et al., "B7.1 and Cytokines: Synergy in cancer gene therapy," *Adv Exp Med Biol.*, 465:381-390, 2000.
Kusmartsev et al., "Gr-1+ myeloid cells derived from tumor-bearing mice inhibit primary T cell activation induced through CD3/CD28 costimulation," *J Immunol.*, 165(2):779-785, Jul. 15, 2000.
Kwon et al., "4-1BB: Still in the Midst of Darkness," *Mol Cells.*, 10(2):119-126, Apr. 30, 2000.
LaBaer, "So, you want to look for biomarkers (introduction to the special biomarkers issue)," *J Proteome Res.*, 4(4):1053-1059, Jul.-Aug. 2005.
Larrubia et al., "Bim-mediated apoptosis and PD-1/PD-L1 pathway impair reactivity of PD1(+)/CD127(−) HCV-specific CD8(+) cells targeting the virus in chronic hepatitis C virus infection," *Cell Immunol.*, 269(2):104-114, Epub Mar. 17, 2011.
Latchman et al., "PD-L2 is a second ligand for PD-1 and inhibits T cell activation," *Nat Immunol.*, 2(3):261-268, Mar. 2001.
Lawson et al., "Treatment of murine lupus with cDNA encoding IFN-gammaR/Fc," *J Clin Invest.*, 106(2):207-215, Jul. 2000.
Lee et al., "Survivin expression and its clinical significance in pancreatic cancer," *BMC Cancer.* 5:127, Oct. 4, 2005.
Lee et al., "Increased vaccine-specific T cell frequency after peptide-based vaccination correlates with increased susceptibility to in vitro stimulation but does not lead to tumor regression," *J Immunol.*, 163(11):6292-6300, Dec. 1, 1999.
Leibovich et al., "Prediction of progression after radical nephrectomy for patients with clear cell renal cell carcinoma: a stratification tool for prospective clinical trials," *Cancer*, 97(7):1663-1671, Apr. 1, 2003.
Lenardo et al., "Mature T lymphocyte apoptosis—immune regulation in a dynamic and unpredictable antigenic environment," *Annu Rev Immunol.*, 17:221-253, 1999.
Lenschow et al., "CD28/B7 system of T cell costimulation," *Annu Rev Immunol.*, 14:233-258, 1996.
Levitt, "Accurate modeling of protein conformation by automatic segment matching," *J Mol Biol.*, 226(2):507-533, Jul. 20, 1992.
Lewinski, et al., Retroviral DNA integration: viral and cellular determinants of target-site selection, PLoS Pathog. 2(6):e60, Epub Jun. 23, 2006.
Lewis, "PCR's Competitors Are Alive and Well and Moving Rapidly Towards Commercialization," *Genetic Engineering News*, vol. 12, 3 pages, 1992.
Li et al., "Anti-programmed death-1 synergizes with granulocyte macrophage colony-stimulating factor—secreting tumor cell immunotherapy providing therapeutic benefit to mice with established tumors," *Clin Cancer Res.*, 15(5):1623-1634, Epub Feb. 10, 2009.
Li et al., "Gemcitabine and arabinosylcytosin pharmacogenomics: genome-wide association and drug response biomarkers," *PLoS One.*, 4(11):e7765, Nov. 9, 2009.
Liang et al., "Autoantibody responses and pathology regulated by B7-1 and B7-2 costimulation in MRL/lpr lupus," *J Immunol.*, 165(6):3436-3443, Sep. 15, 2000.
Linsley et al., "Binding of the B cell activation antigen B7 to CD28 costimulates T cell proliferation and interleukin 2 mRNA accumulation" *J Exp Med.*, 173(3):721-730, Mar. 1, 1991.
Linsley et al., "Extending the B7 (CD80) gene family," *Protein Sci.*, 3(8):1341-1343, Aug. 1994.
Linsley et al., "T-cell antigen CD28 mediates adhesion with B cells by interacting with activation antigen 87188-1," *Proc Natl Acad Sci U S A.*, 87(13):5031-5035, Jul. 1990.
Liu et al., "B7DC/PDL2 promotes tumor immunity by a PD-1-independent mechanism," *J Exp Med.*, 197(12):1721-1730, Jun. 16, 2003.
Liu et al., "B7-H3 silencing increases paclitaxel sensitivity by abrogating Jak2/Stat3 phosphorylation," *Mol Cancer Ther.*, 10(6):960-971, Epub Apr. 25, 2011.
Liu et al., "Endogenous tumor-reactive CD8+ T cells are differentiated effector cells expressing high levels of CD11a and PD-1 but are unable to control tumor growth," *Oncoimmunology.*, 2(6):e23972, Epub Jun. 6, 2013.
Liu et al., "Fas-mediated apoptosis causes elimination of virus-specific cytotoxic T cells in the virus-infected liver," *J Immunol.*, 166(5):3035-3041, Mar. 1, 2001.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway," *Blood*, 110(1):296-304, Epub Mar. 15, 2007.
Lonberg et al., "Antigen-specific human antibodies from mice comprising four distinct genetic modifications," *Nature*, 368(6474):856-859, Apr. 28, 1994.
Losman et al., "Baboon anti-idiotype antibodies mimic a carcinoembryonic antigen epitope," *Int J Cancer.*, 46(2):310-314, Aug. 15, 1990.
Lu et al., "EGF-IL-18 fusion protein as a potential anti-tumor reagent by induction of immune response and apoptosis in cancer cells," *Cancer Lett.*, 260(1-2):187-197, Epub Dec. 21, 2007.
Luciano et al., "Phosphorylation of Bim-EL by Erk1/2 on serine 69 promotes its degradation via the proteasome pathway and regulates its proapoptotic function," *Oncogene.*, 22(43):6785-6793, Oct. 2, 2003.
Luettig et al., "Naive and memory T lymphocytes migrate in comparable numbers through normal rat liver: activated T cells accumulate in the periportal field," *J Immunol.*, 163(8):4300-4307, Oct. 15, 1999.
Ma et al., "The DNA-dependent protein kinase catalytic subunit phosphorylation sites in human Artemis," *J Biol Chem.*, 280(40):33839-33846, Epub Aug. 10, 2005.
Ma et al., "The Role of PD-1 Ligand in Immune Evasion by Breast Cancer," Dana-Farber Cancer Institute Annual Summary Report May 1, 2002-Apr. 30, 2005, pp. 5-6, 9, 11, report date: May 2005.

(56) References Cited

OTHER PUBLICATIONS

Mah et al., "gammaH2AX: a sensitive molecular marker of DNA damage and repair," *Leukemia*, 24(4):679-686, Epub Feb. 4, 2010.
Mahotka et al., "Distinct in vivo expression patterns of survivin splice variants in renal cell carcinomas," *Int J Cancer*, 100(1):30-36, Jul. 1, 2002.
Mann et al., "Construction of a retrovirus packaging mutant and its use to produce helper-free defective retrovirus" *Cell*, 33(1):153-159, May 1983.
Martin et al. "Combination gene therapy with CD86 and the MHc Class II transactivator in the control of lung tumor growth," *J Immunol.*, 162(11):6663-6670, Jun. 1, 1999.
Mathiowitz et al., "Morphology of poly anhydride microsphere delivery system." *Scanning Microsc.*, 4(2):329-340, Jun. 1990.
Mathiowitz et al., "Polyanhydride microspheres as drug carriers. I. Hot-melt microencapsulation," *J. Controlled Release*, 5(1):13-22, Jun. 1, 1987.
Mathiowitz et al., "Polyanhydride microspheres. IV. Morphology and characterization of systems made by spray drying," *J. Anni. Polymer Sci.* 45(1): 125-134, May 5, 1992.
Mathiowitz, Novel microcapsules for delivery systems, *Reactive Polymers*, 6(2):275-283, Oct. 31, 1987.
Mathiowitz, "Polyanhydride microspheres as drug carriers, II. Microencapsulation by solvent removal," *J. Appl. Polymer Sci.*, 35(3): 755-774, Feb. 20, 1988.
Mayo Clinic, "Mayo Clinic Discovers Potential Marker for Aggressive Kidney Cancer," Science Daily, Retrieved from the Internet: <URL: https://www.sciencedaily.com/releases/2004/11/041130200858.htm>, 2 pages, Dec. 9, 2004.
McCubrey et al., "Roles of the Raf/MEK/ERK pathway in cell growth, malignant transformation and drug resistance," *Biochim Biophys Acta.*, 1773(8):1263-1284, Epub Oct. 7, 2006.
McLachlin et al., "Retroviral-mediated gene transfer," *Prog Nucleic Acid Res Mol Biol.*, 38:91-135, 1990.
Mehal et al., "Antigen presentation by liver cells controls intrahepatic T cell trapping, whereas bone marrow-derived cells preferentially promote intrahepatic T cell apoptosis," *J Immunol.*, 167(2):667-673, Jul. 15, 2001.
Mehal et al., "TCR ligation on CD8+ T cells creates double-negative cells in vivo," *J Immunol.*, 161(4):1686-1693, Aug. 15, 1998.
Melero et al., "Amplification of tumor immunity by gene transfer of the co-stimulatory 4-1BB ligand: synergy with the CD28 co-stimulatory pathway," *Eur J Immunol.*, 28(3):1116-1121, Mar. 1998.
Melero et al., "Monoclonal antibodies against the 4-1BB T-cell activation molecule eradicate established tumors," *Nat Med.*, 3(6):682-685, Jun. 1997.
Melero et al., "NK1.1 cells express 4-1BB (CDw137) costimulatory molecule and are required for tumor immunity elicited by anti-4-1BB monoclonal antibodies," *Cell Immunol.*, 190(2):167-172, Dec. 15, 1998.
Melief et al., "Strategies for immunotherapy of cancer," *Advances in immunology*, 75:235-282, Jan. 1, 2000.
Mendez-Fernandez et al., "Clearance of Theiler's virus infection depends on the ability to generate a CD8+ T cell response against a single immunodominant viral peptide," *Eur J Immunol.*, 33(9):2501-2510, Sep. 2003.
Merrill, "Emergence of targeted immune therapies for systemic lupus " *Expert Opin Emerg Drugs.*, 10(1):53-65, Feb. 2005.
Merritt et al., "Activation of p38 mitogen-activated protein kinase in vivo selectively induces apoptosis of CD8(+) but not CD4(+) T cells," *Mol Cell Biol.*, 20(3):936-946, Feb. 2000.
Metzler et al., "Solution structure of human CTLA-4 and delineation of a CD80/CD86 binding site conserved in CD28," *Nat Struct Biol.*, 4(7):527-531, Jul. 1997.
Miller et al., "Gene transfer by retrovirus vectors occurs only in cells that are actively replicating at the time of infection," *Mol Cell Biol.*, 10(8):4239-4242, Aug. 1990.

Miller et al., "Generation of helper-free amphotropic retroviruses that transduce a dominant-acting, methotrexate-resistant dihydrofolate reductase gene," *Mol Cell Biol.*, 5(3):431-437, Mar. 1985.
Miller et al., "Redesign of retrovirus packaging cell lines to avoid recombination leading to helper virus production," *Mol Cell Biol.*, 6(8):2895-2902, Aug. 1986.
Miller, "Human gene therapy comes of age," *Nature*, 357(6378):455-460, Jun. 11, 1992.
Misquitta et al., "Targeted disruption of gene function in *Drosophila* by RNA interference (RNA-i): A role for nautilus in embryonic somatic muscle formation," *Proc Natl Acad Sci U S A.*, 96(4):1451-1456, Feb. 16, 1999.
Mizuhara et al., "T cell activation-associated hepatic injury: mediation by tumor necrosis factors and protection by interleukin 6," *J Exp Med.*, 179(5):1529-1537, May 1, 1994.
Mohan et al., "Interaction between CD40 and its ligand gp39 in the development of murine lupus nephritis," *J Immunol.*, 154(3):1470-1480, Feb. 1, 1995.
Montesano et al, "Genetic alterations in esophageal cancer and their relevance to etiology and pathogenesis: a review," *Int J Cancer.*, 69(3):225-235, Jun. 21, 1996.
Morrison et al., "Chimeric human antibody molecules: mouse antigen-binding domains with human constant region domains," *Proc Natl Acad Sci U S A.*, 81(21):6851-6855, Nov. 1984.
Morse et al., "Abnormalities induced by the mutant gene lpr: expansion of a unique lymphocyte subset," *J Immunol.*, 129(6):2612-2615, Dec. 1982.
Moss, "Poxvirus expression vectors," *Curr Top Microbiol Immunol.*, 158:25-38, 1992.
Moss, "Poxvirus vectors: cytoplasmic expression of transferred genes," *Curr Opin Genet Dev.*, 3(1):86-90, Feb. 1993.
Moss, "Use of vaccinia virus as an infectious molecular cloning and expression vector " *Gene Amplif Anal.*, 3:201-213, 1983.
Moss, "Vaccinia virus vectors," Biotechnology, 20:345-362, 1992.
Moss, "Vaccinia virus: a tool for research and vaccine development," *Science*, 252(5013):1662-1667, Jun. 21, 1991.
Motzer et al., "Renal Cell Carcinoma," *N Engl J Med.*, 335(12):865-75, Sep. 19, 1996.
Mukherjee et al., "DNA-PK phosphorylates histone H2AX during apoptotic DNA fragmentation in mammalian cells," *DNA Repair (Amst).* 5(5):575-590, Epub Mar. 29, 2006.
Muyldernaans, "Single domain camel antibodies: current status," *J Biotechnol.*, 74(4):277-302, Jun. 2001.
Nabel et al., "Recombinant gene expression in vivo within endothelial cells of the arterial wall," *Science*, 244(4910):1342-1344, Jun. 16, 1989.
National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/detection/tumor-markers/print>, 8 pages.
Nechiporuk et al., "The mouse SCA2 gene: cDNA sequence, alternative splicing and protein expression," *Hum Mol Genet.*, 7(8):1301-1309, Aug. 1998.
Needleman et al., "A general method applicable to the Search for similarities in the amino acid sequence of two proteins," J Mol Biol. 48(3):443-453, Mar. 1970.
Nelson et al., "Tumor progression despite efficient tumor antigen cross-presentation and effective "arming" of tumor antigen-specific CTL," *J Immunol.*, 166(9):5557-5566, May 1, 2001.
Neves et al., "Surgical treatment of renal cancer with vena cava extension," *Br J Urol.*, 59(5):390-395, May 1987.
Newmark et al., "Preparation and properties of adducts of streptokinase and streptokinase-plasmin complex with poly ethylene glycol and pluronic polyol F38," *J Appl Biochem.*, 4:185-189, 1982.
Nicolau et al., "In vivo expression of rat insulin after intravenous administration of the liposome-entrapped gene for rat insulin I," *Proc Natl Acad Sci U S A.*, 80(4):1068-1072, Feb. 1983.
Nielsen et al., "Melanoma vaccines: the paradox of T cell activation without clinical response," *Cancer Chemother Pharmacol.*, 46 Suppl:S62-S66, 2000.
Nielsen et al., "Peptide nucleic acid (PNA). A DNA mimic with a peptide backbone " *Bioconjug Chem.*, 5(1):3-7, Jan.-Feb. 1994.

(56) References Cited

OTHER PUBLICATIONS

Nielsen et al., "Sequence-selective recognition of DNA by strand displacement with a thymine-substituted polyamide," *Science*, 254(5037):1497-1500, Dec. 6, 1991.
Nishimura et al., "Autoimmune dilated cardiomyopathy in PD-1 receptor-deficient mice," *Science*, 291(5502):319-322, Jan. 12, 2001.
Nishimura et al., "Development of lupus-like autoimmune diseases by disruption of the PD-1 gene encoding an ITIM motif-carrying immunoreceptor," *Immunity*, 11(2):141-151, Aug. 1999.
Nishimura et al., "Immunological studies on PD-1-deficient mice: implication of PD-1 as a negative regulator for B cell responses," *Int Immunol.*, 10(10):1563-1572, Oct. 1998.
Nisonhoff et al., "Separation of univalent fragments from the bivalent rabbit antibody molecule by reduction of disulfide bonds," *Arch Biochem Biophys.*, 89:230-244, Aug. 1960.
Ohigashi et al., "Clinical significance of programmed death-1 ligand-1 and programmed death-1 ligand-2 expression in human esophageal cancer," *Clin Cancer Res.*, 11(8):2947-2953, Apr. 15, 2005.
Okazaki et al., "PD-1 and PD-1 ligands: from discovery to clinical application," *Int Immunol.*, 19(7):813-824, Epub Jul. 2, 2007.
Opferman al., "Linear differentiation of cytotoxic effectors into memory T lymphocytes " *Science*, 283(5408):1745-1748, Mar. 12, 1999.
O'Reilly et al., "MEK/ERK-mediated phosphorylation of Bim is required to ensure survival of T and B lymphocytes during mitogenic stimulation," *J Immunol.*, 183(1):261-269, Jul. 1, 2009.
Orlandi et al., "Cloning immunoglobulin variable domains for expression by the polymerase chain reaction," *Proc Natl Acad Sci U S A.*, 86(10):3833-3837, May 1989.
Ostrov et al., "Structure of murine CTLA-4 and its role in modulating T cell responsiveness," *Science*, 290(5492):816-819, Oct. 27, 2000.
Ozkaynak et al., "Programmed death-1 targeting can promote allograft survival," *J Immunol.*, 169(11):6546-6553, Dec. 1, 2002.
Panda et al., "ATM and the catalytic subunit of DNA-dependent protein kinase activate NF-kappaB through a common MEK/extracellular signal-regulated kinase/p90(rsk) signaling pathway in response to distinct forms of DNA damage," *Mol Cell Biol.*, 24(5):1823-1835, Mar. 2004.
Pantuck et al., "The changing natural history of renal cell carcinoma," *J Urol.*, 166(5):1611-1623, Nov. 2001.
Pardoll, "Spinning molecular immunology into successful immunotherapy," *Nat Rev Immunol.*, 2(4):227-238, Apr. 2002.
Pardoll., "The Blockade of Immune Checkpoints in Cancer Immunotherapy " *Nat Review.*, 12:252-264, Apr. 2012.
Park et al., "B7-H1/CD80 interaction is required for the induction and maintenance of peripheral T-cell tolerance," *Blood.*, 116(8):1291-1298, Epub May 14, 2010.
Parker et al., "Potential utility of uroplakin III, thrombomodulin, high molecular weight cytokeratin, and cytokeratin 20 in noninvasive, invasive, and metastatic urothelial (transitional cell) carcinomas," *Am J Surg Pathol.*, 27(1):1-10, Jan. 2003.
Parsa et al., "Loss of tumor suppressor PTEN function increases B7-H1 expression and immunoresistance in glioma," *Nat Med.*, 13(1):84-88, Epub Dec. 10, 2006.
Paterson et al., "The PD-L1 :B7-1 pathway restrains diabetogenic effector T cells in vivo," *J Immunol.*, 187(3):1097-1105, Aug. 1, 2011.
Patsoukis et al., "Selective effects of PD-1 on Akt and Ras pathways regulate molecular components of the cell cycle and inhibit T cell proliferation," *Sci Signal.*, 5(230):ra46, Jun. 26, 2012.
Pavelko et al., "The epitope integration site for vaccine antigens determines virus control while maintaining efficacy in an engineered cancer vaccine," *Mol Ther.*, 21(5):1087-1095, Epub Apr. 9, 2013.
Peach et al., "Both extracellular immunoglobulin-like domains of CD80 contain residues critical for binding T cell surface receptors CTLA-4 and CD28," *J Biol Chem.*, 270(36):21181-21187, Sep. 8, 1995.

Pece and Gutkind, "Signaling from E-cadherins to the MAPK pathway by the recruitment and activation of epidermal growth factor receptors upon cell-cell contact formation," *J Biol Chem.*, 275(52):41227-41233, Dec. 29, 2000.
Pedraza-Alva et al., "Activation of p38 MAP kinase by DNA double-strand breaks in V(D)J recombination induces a G2/M cell cycle checkpoint," *EMBO J.*, 25(4):763-773, Epub Feb. 2, 2006.
Peghini et al, [Immunophaenotyping in the diagnosis of lymphoma]. *Praxis (Bern 1994)* 93(41):1687-1692, Oct. 6, 2004, Article in German, English abstract included.
Pei et al., "FKBP51 affects cancer cell response to chemotherapy by negatively regulating Akt," *Cancer Cell.*, 16(3):259-266, Sep. 8, 2009.
Penia et al., "Two essential regulatory elements in the human interferon gamma promoter confer activation specific expression in T cells," *J Exp Med.*, 178(5):1483-1496, Nov. 1, 1993.
Perriman et al., "Effective ribozyme delivery in plant cells," *Proc Natl Acad Sci U S A.*, 92(13):6175-6179, Jun. 20, 1995
Petroff et al., "B7 family molecules: novel immunomodulators at the maternal-fetal interface," *Placenta*, 23 Suppl A:S95-101, Apr. 2002.
Piccini, "Vaccinia: virus, vector, vaccine," *Adv Virus Res.*, 34:43-64, 1988.
Plückthun et al., "Expression of functional antibody Fv and Fab fragments in *Escherichia coli*," *Methods Enzymol.*, 178:497-515, 1989.
Plückthun, "Antibodies from *Escherichia coli*." The Pharmacology of Monoclonal Antibodies. Handbook of Experimental Pharmacology, Springer Berlin Heidelberg, pp. 269-315, 1994.
Poirier, "Protective immunity evoked by oral administration of attenuated aroA *Salmonella typhimurium* expressing cloned streptococcal M protein," *J Exp Med.*, 168(1):25-32, Jul. 1, 1988.
Pollok et al., "4-1BB T-cell antigen binds to mature B cells and macrophages, and costimulates anti-mu-primed splenic B cells," *Eur J Immunol.*, 24(2):367-374, Feb. 1994.
Pollok et al., "Inducible T Cell Antigen 4-1BB," *J Immunol.*, 150(3):771-781, Feb. 1, 1993.
Ponder et al., "Tertiary templates for proteins. Use of packing criteria in the enumeration of allowed sequences for different structural classes," *J Mol Biol.*, 193(4):775-791, Feb. 20, 1987.
Porter, "The hydrolysis of rabbit γ-globulin and antibodies with crystalline papain," *Biochem J.*, 73:119-126, Sep. 1959.
Powell et al., "Compendium of excipients for parenteral formulations," *PDA J Pharm Sci Technol.*, 52(5):238-311, Sep.-Oct. 1998.
Prasad et al., "B7S1, a novel B7 family member that negatively regulates T cell activation," *Immunity*, 18(6):863-873, Jun. 2003.
Presta, "Antibody engineering," *Curr Opin Biotechnol.*, 2(4):593-596, 1992.
Presta, "Antibody engineering," *Curr Opin Biotechnol.*, 3(4):394-398, Aug. 1992.
Prévost-Blondel et al., "Tumor-infiltrating lymphocytes exhibiting high ex vivo cytolytic activity fail to prevent murine melanoma tumor growth in vivo," *J Immunol.*, 161(5):2187-2194, Sep. 1, 1998.
Pulko et al., "B7-hl expressed by activated CD8 T cells is essential for their survival," *J Immunol.*, 187(11):5606-5614, Epub Oct. 24, 2011.
Pulko et al., "TLR3-stimulated dendritic cells up-regulate B7-H1 expression and influence the magnitude of CD8 T cell responses to tumor vaccination," *J Immunol.*, 183(6):3634-3641, Epub. Aug. 26, 2009.
Qi et al., "Evidence that Ser87 of BimEL is phosphorylated by Akt and regulates BimEL apoptotic function," *J Biol Chem.*, 281(2):813-823, Epub Nov. 10, 2005.
Radhakrishnan et al., "Dendritic cells activated by cross-linking B7-DC (PD-L2) block inflammatory airway disease," *J Allergy Clin Immunol.*, 116(3):668-674, Sep. 2005.
Rajewsky et al., "Genetics, expression, 1983 and function of idiotypes," *Annu Rev Immunol.*, 1:569-607, 1983.
Rathmell et al., "The central effectors of cell death in the immune system," *Annu. Rev. Immunol..*, 17:781-828, 1999.

(56) References Cited

OTHER PUBLICATIONS

Razi-Wolf, "Expression and function of the murine B7 antigen, the major costimulatory molecule expressed by peritoneal exudate cells," *Proc Natl Acad Sci U S A.*, 89(9):4210-4214, May 1, 1992.
Renauld et al., "Expression cloning of the murine and human interleukin 9 receptor cDNAs," *Proc. Natl Acad Sci U S A.*, 89(12):5690-5694, Jun. 15, 1992.
Riechmann et al., "Reshaping human antibodies for therapy," *Nature*, 332(6162):323-327, Mar. 24, 1998.
Rincon et al., "JNK and p38 MAP kinases in CD4+ and CD8+ T cells," *Immunol Rev.*, 192:131-142, Apr. 2003.
Ritz et al., "Bioassay analysis using R," *J Stat Softw.*, 12(5):1-22, Jan. 19, 2005.
Rivoltini et al., "Immunity to cancer: attack and escape in T lymphocyte-tumor cell interaction," *Immunol Rev.*, 188:97-113, Oct. 2002.
Robison-Cox, "Multiple estimation of concentrations in immunoassay using logistic models," *J Immunol Methods*, 186(1):79-88, Oct. 12, 1995.
Romano et al., "Quelling: transient inactivation of gene expression in Neurospora crassa by transformation with homologous sequences," *Mol Microbiol.*, 6(22):3343-3353, Nov. 1992.
Romero et al., "Ex vivo staining of metastatic lymph nodes by class I major histocompatibility complex tetramers reveals high numbers of antigen-experienced tumor-specific cytolytic T lymphocytes," *J Exp Med.*, 188(9):1641-1650, Nov. 2, 1998.
Rosenberg, "Progress in human tumor immunology and immunotherapy," *Nature*, 411(6835):380-384, May 17, 2001.
Rosenfeld et al., "Adenovirus-mediated transfer of a recombinant alpha 1-antitrypsin gene to the lung epithelium in vivo," *Science*, 252(5004):431-434, Apr. 19, 1991.
Rousseaux et al, "Optimal conditions for the preparation of proteolytic fragments from monoclonal IgG of different rat IgG subclasses," *Methods Enzymol.*, 121:663-669, 1986.
Rowe et al., "PDL-1 blockade impedes T cell expansion and protective immunity primed by attenuated Listeria monocytogenes," *J Immunol.*, 180(11):7553-7557, Jun. 1, 2008.
Sadoff, "Oral *Salmonella typhimurium* vaccine expressing circumsporozoite protein protects against malaria," *Science*, 240(4850):336-338, Apr. 15, 1988.
Salama et al., "Critical role of the programmed death-1 (PD-1) pathway in regulation of experimental autoimmune encephalomyelitis," *J Exp Med.*, 198(1):71-78, Jul. 7, 2003.
Salib et al., "Utilization of sodium alginatein drug microencapsulation," *Pharm Ind.*, 40(11 a):1230-1234,1978.
Salih et al., "4-1 BB ligand—just another costimulating molecule?," *Int J Clin Pharmacol Ther.*, 40(8):348-353, Aug. 2002.
Salih et al., "The role of leukemia-derived B7-H1 (PD-L1) in tumor-T-call interactions in humans," *Exp Hematol.*, 34(7):888-894, Jul. 2006.
Salomon et al., "Complexities of CD28/B7: CTLA-4 costimulatoiy pathways in autoimmunity and transplantation," *Annu Rev Immunol.*, 19:225-252, 2001.
Samulski, "Targeted integration of adenoassoc ated virus (AAV) into human chromosome 19," *EMBO J.*, 10(12):3941-3950, Dec. 1991.
Sandhu, "Protein engineering of antibodies," *Crit Rev Biotechnol.*, 12(5-6):437-462, 1992.
Sanni et al., "Evolution of aminoacyl-tRNA synthetase quaternary structure and activity: *Saccharomyces cerevisiae* mitochondrial phenylalanyl-tRNA synthetase " *Proc Natl Acad Sci U S A.*, 88(19):8387-8391, Oct. 1, 1991.
Sarbassov et al., "Phosphorylation and regulation of Akt/PKB by the rictor-mTOR complex," *Science*, 307(5712):1098-1101, Feb. 18, 2005.
Sawhney et al., "Bioerodible hydrogels based on photopolymerized poly(ethylene glycol)-co-poly(.alpha.-hydroxy acid) diacrylate macromers," *Macromolecules*, 26(4):581-587, Jul. 1993.

Schafer, "Induction of a cellular immune response to a foreign antigen by a recombinant Listeria monocytogenes vaccine," *J Immunol.*, 149(1):53-59, Jul. 1, 1992.
Schmid et al, "Expression of AMPA receptor subunit flip/flop splice variants in the rat auditory brainstem and inferior colliculus," *J Comp Neurol.*, 430(2):160-171, Feb. 5, 2001.
Schurich et al., "The third signal cytokine IL-12 rescues the anti-viral function of exhausted HBV-specific CD8 T cells," *PLoS Pathog.*, 9(3):e1003208, Epub Mar. 14, 2013.
Schwartz et al, "Costimulation of T lymphocytes: the role of CD28, CTLA-4, and B7/BBI in interluekin-2 production and immunotherapy," *Cell*, 71(7):1065-1068, Dec. 24, 1992.
Schwartz et al., "Structural basis for co-stimulation by the human CTLA-4/B7-2 complex," *Nature*,. 410(6828):604-608, Mar. 29, 2001.
Schwartz et al., "Structural mechanisms of costimulation," *Nat Immunol.* 3(5):427-434, May 2002.
Sedletska et al., "Cisplatin is a DNA-damaging antitumour compound triggering multifactorial biochemical responses in cancer cells: importance of apoptotic pathways " *Curr Med Chem Anticancer Agents.*, 5(3):251-265, May 2005.
Selenko-Gebauer et al., "B7-H1 (programmed death-1 ligand) on dendritic cells is involved in the induction and maintenance of T cell anergy," *J Immunol.*, 170(7):3637-3644, Apr. 1, 2003.
Seo et al., "Blockade of endogenous B7-H1 suppresses antibacterial protection after primary Listeria monocytogenes infection," *Immunology*, 123(1):90-99, Epub Oct. 25, 2007.
Shaknovich et al., "The promyelocytic leukemia zinc finger protein affects myeloid cell growth, differentiation, and apoptosis," *Mol Cell Biol.*, 18(9):5533-5545, Sep. 1998.
Shao et al., "Deficiency of the DNA repair enzyme ATM in rheumatoid arthritis," *J Exp Med.*, 206(6):1435-1449, Epub May 18, 2009.
Shao et al., "DNA-dependent protein kinase catalytic subunit mediates T-cell loss in rheumatoid arthritis," *EMBO Mol Med.*, 2(10):415-427, Oct. 2010.
Sharon et al., "Preparation of Fv fragment from the mouse myeloma XRPC-25 immunoglobulin possessing anti-dinitrophenyl activity," *Biochemistry*, 15(7):1591-1594, Apr. 6, 1976.
Sheather, "Density Estimation," *Statistical Sci.*, 19(4):588-597, 2004.
Shin et al., "Cooperative B7-1/2 (CD80/CD86) and B7-DC costimulation of CD4+ T cells independent of the PD-1 receptor," *J Exp Med.*, 198(1):31-38, Jul. 7, 2003.
Sica et al., "B7-H4, a molecule of the B7 family, negatively regulates T cell immunity," *Immunity.*, 18(6):849-861, Jun. 2003.
Sica et al., "Biochemical and immunological characteristics of 4-1BB (CD137) receptor and ligand and potential applications in cancer therapy," *Arch Immunol Ther Exp (Warsz).* 47(5):275-279, 1999.
Siddiqui et al., "Tumor-infiltrating Foxp3-CD4+CD25+ T cells predict poor survival in renal cell carcinoma," *Clin Cancer Res.*, 13(7):2075-2081, Apr. 1, 2007.
Simon et al., "B7-h4 is a novel membrane-bound protein and a candidate serum and tissue biomarker for ovarian cancer," *Cancer Res.*, 66(3):1570-1575, Feb. 1, 2006.
Singer et al., "Optimal humanization of 1B4, an Anti-CD18 murine monoclonal antibody, is achieved by correct choice of human v-region framework sequences," *J Immunol.*, 150(7).2844-2857, Apr. 1, 1993.
Skerra et al., "Assembly of a functional immunoglobulin Fv fragment in *Escherichia coli*," *Science*, 240(4855):1038-1041, May 20, 1988.
Skolnick et al., "From genes to protein structure and function: novel applications of computational approaches in the genomic era," *Trends Biotechnol.*, 18(1):34-39, Jan. 2000.
Smith et al., "Pulmonary deposition and clearance of aerosolized alpha-1-proteinase inhibitor administered to dogs and to sheep," *J Clin Invest.*, 84(4):1145-1154, Oct. 1989.
Sneller et al., "A novel lymphoproliferative/autoimmune syndrome resembling murine 1pr/gld disease,"*J Clin Invest.*, 90(2):334-341, Aug. 1992.

(56) References Cited

OTHER PUBLICATIONS

Solier et al., "Death receptor-induced activation of the Chk2- and histone H2AX-associated DNA damage response pathways," *Mol Cell Biol.*, 29(1):68-82, Epub Oct. 27, 2008.
Sorge et al., "Amphotropic retrovirus vector system for human cell gene transfer," *Mol Cell Biol.*, 4(9):1730-1737, Sep. 1984.
Soriano, "Targeted and nontargeted liposomes for in vivo transfer to rat liver cells of a plasmid containing the preproinsulin I gene," *Proc Natl Acad Sci U S A.*, 80(23):7128-7131, Dec. 1983.
Soubeyrand et al., "Artemis phosphorylated by DNA-dependent protein kinase associates preferentially with discrete regions of chromatin," *J Mol Biol.*, 358(5):1200-1211, Epub Mar. 20, 2006.
Stammers et al., "BTL-II: A polymorphic locus with homology to the butyrolphilin gene family, located at the border of the major histocompatibility complex class II and class III regions in human and mouse," *Immunogenetics*, 51(4-5):373-382, Apr. 2000.
Stamper et al., "Crystal structure of the B7-1/CTLA-4 complex that inhibits human immune responses," *Nature*, 410(6828):608-611, Mar. 29, 2001.
Strome et al., "B7-H1 blockade augments adoptive T-cell immunotherapy for squamous cell carcinoma," *Cancer Res.*, 63(19):6501-6505, Oct. 1, 2003.
Strome et al., "Enhanced therapeutic potential of adoptive immunotherapy by in vitro CD28/4-1BB costimulation of tumor-reactive T cells against a poorly immunogenic, major histocompatibility complex class I-negative A9P melanoma," *J Immunothe.*, 23(4):430-437, Jul.-Aug. 2000.
Subudhi et al., "Local expression of B7-H1 promotes organ-specific autoimmunity and transplant rejection," *J Clin Invest.*, 113(5):694-700, Mar. 2004.
Suda et al., "Why do defects in the Fas-Fas ligand system cause autoimmunity?" *J Allergy Clin Immunol.*, 100(6 Pt 2):S97-S101, Dec. 1997.
Summerton et al., "Morpholino antisense oligomers: design, preparation, and properties, "*Antisense Nucleic Acid Drug Dev.*, 7(3):187-195, Jun. 1997.
Sun et al., "Administration of agonistic anti-4-1BB monoclonal antibody leads to the amelioration of experimental autoimmune encephalomyelitis," *J Immunol.*, 168(3):1457-1465, Feb. 1, 2002.
Sun et al., "Costimulatory molecule-targeted antibody therapy of a spontaneous autoimmune disease," *Nat Med.*, 8(12):1405-1413, Epub Nov. 11, 2002.
Sun et al., "Signaling of 4-1BB Leads to Amelioration of Experimental Autoimmune Encephalomyelitis," *FASEB J.*, vol. 5, p. A1210 Abstract 950.9, 2001.
Sutter et al., "Nonreplicating vaccinia vector efficiently expresses recombinant genes "*Proc Natl Acad Sci U S A.*, 89(22):10847-10851, Nov. 15, 1992.
Suzuki et al., "T cell-specific loss of Pten leads to defects in central and peripheral tolerance," *Immunity*, 14(5):523-534, May 2001.
Suzuki et al., "The dual functions of fas ligand in the regulation of peripheral CD8+ and CD4+ T cells," *Proc Natl Acad Sci U S A.*, 97(4):1707-1712, Feb. 15, 2000.
Swallow et al., "B7h, a novel costimulatory homolog of B7.1 and B7.2, is induced by TNFalpha," *Immunity*, 11(4):423-432, Oct. 1999.
Takahashi et al., "Cutting edge: 4-1BB is a bona fide CD8 T cell survival signal," *J Immunol.*, 162(9):5037-5040, May 1, 1999.
Takeda et al., "Critical contribution of liver natural killer T cells to a murine model of hepatitis," *Proc Natl Acad Sci U S A.*, 97(10):5498-5503, May 9, 2000.
Tamura et al., "B7-H1 costimulation preferentially enhances CD28-indepenent T-helper cell function," *Blood*, 97(6):1809-1816, Mar. 15, 2001.
Tamura et al., "Marrow stromal cells induce B7-H1 expression on myeloma cells, generating aggressive characteristics in multiple myeloma," *Leukemia*, 27(2):464-472, 2013.
Taylor et al., "Human immunoglobulin transgenes undergo rearrangement, somatic mutation and class switching in mice that lack endogenous IgM," *Int Immunol.*, 6(4):579-591, Apr. 1994.
Tazi-Ahnini et al., "Cloning, localization, and structure of new members of the butyrophilin gene family in the juxtatelomenc region of the major histocompatibility complex," *Immunogenetics.*, 47(1):55-63, 1997.
Temin, "Safety considerations in somatic gene therapy of human disease with retrovirus vectors," *Hum Gene Ther.*, 1(2):111-123, Summer 1990.
Templeton et al., "Improved DNA: liposome complexes for increased systemic delivery and gene expression," *Nat Biotechnol.*, 15(7):647-652, Jul. 1997.
Theofilopoulos et al., "Tumour necrosis factor and other cytokines in murine lupus " *Ann Rheum Dis.*, 58(suppl 1):I49-55, Nov. 1, 1999.
Theofilopoulos et al., "Etiopathogenesis of Murine SLE," *Immunol Rev.* 55:179-216, 1981.
Thompson et al., "cis-acting sequences required for inducible interleukin-2 enhancer function bind a novel Ets-related protein, Elf-1," *Mol Cell Biol.*, 12(3):1043-1053, Mar. 1992.
Thompson et al., "Costimulatoty B7-H1 in renal cell carcinoma patients: Indicator of tumor aggressiveness and potential therapeutic target," *Proc Natl Acad Sci U S A.*, 101(49):17174-17179. Epub Nov. 29, 2004.
Thompson et al., "Costimulatory molecule B7-H1 in primary and metastatic clear cell renal cell carcinoma," *Cancer*, 104(10):2084-2091, Nov. 15, 2005.
Thompson et al., "Tumor B7-H1 is associated with poor prognosis in renal cell carcinoma patients with long-term follow-up," *Cancer Res.*, 66(7):3381-3385, Apr. 1, 2006.
Tian et al., "The relationship between the down-regulation of DNA-PKcs or Ku70 and the chemosensitization in human cervical carcinoma cell line HeLa," *Oncol Rep.*, 18(4):927-932, Oct. 2007.
Tiegs et al., "A T cell-dependent experimental liver injury in mice inducible by concanavalin A," *J Clin Invest.*, 90(1):196-203, Jul. 1992.
Titomirov, "In vivo electroporation and stable transformation of skin cells of newborn mice by plasmid DNA," *Biochim Biophys Acta.*, 1088(1):131-134, Jan. 17, 1991.
Todd et al., "Transcription of the interleukin 4 gene is regulated by multiple promoter elements," *J Exp Med.*, 177(6):1663-1674, Jun. 1, 1993.
Topalian et al., "Safety, activity, and immune correlates of anti-PD-1 antibody in cancer," *The New England Journal of Medicine.*, 368(26):2443-2454, Jun. 28, 2012.
Townsend et al., "Tumor rejection after direct costimulation of CD8+ T cells by B7-transfected melanoma cells," *Science*, 259(5093):368-370, Jan. 15, 1993.
Trabattoni et al. "B7-H1 is up-regulated in HIV infection and is a novel surrogate marker of disease progression" *Blood*, 101(7):2514-2520, Epub Dec. 5, 2002.
Tringler et al., "B7-h4 is highly expressed in ductal and lobular breast cancer," *Clin Cancer Res.*, 11(5):1842-1848, Mar. 1, 2005.
Tseng et al., "B7-DC, a new dendritic cell molecule with potent costimulatory properties for T cells," *J Exp Med.*, 193(7):839-846, Apr. 2, 2001.
Ueda et al., "Sequence-specific DNA damage induced by reduced mitomycin C and 7-N-(p-hydroxyphenyl)mitomycin C.," *Nucleic Acids Res.*, 12(17):6673-6683, Sep. 11, 1984.
Verhoeyen et al., "Reshaping human antibodies: grafting an antilysozyme activity," *Science*, 239(4847):1534-1536, Mar. 25, 1988.
Veuger et al., "Radiosensitization and DNA repair inhibition by the combined use of novel inhibitors of DNA-dependent protein kinase and poly(ADP-ribose) polymerase-1," *Cancer Res.*, 63(18):6008-6015, Sep. 15, 2003.
Vinay et al., "Role of 4-1BB in immune responses," *Semin Immunol.*, 10(6):481-489, Dec. 1998.
Wahl et al., "Improved radioimaging and tumor localization with monoclonal F(ab')2" *J Nucl Med.*, 24(4):316-25, Apr. 1983.
Walunas et al., "CTLA-4 ligation blocks CD28-dependent T cell activation," *J Exp Med.*, 183(6):2541-2550, Jun. 1, 1996.
Wang et al., "Costimulation of T cells by B7-H2, a B7-like molecule that binds ICOS," *Blood*, 96(8):2808-2813, Oct. 15, 2000.

(56) References Cited

OTHER PUBLICATIONS

Wang et al., "Doxorubicin induces apoptosis in normal and tumor cells via distinctly different mechanisms. intermediacy of H(2)O(2)- and p53-dependent pathways," *J Biol Chem.*, 279(24):25535-25543, Epub Mar. 30, 2004.
Wang et al., "Ligand binding sites of inducible costimulator and high avidity mutants with improved function," *J Exp Med.*, 195(8):1033-1041, Apr. 15, 2002.
Wang et al., "Molecular modeling and functional mapping of B7-H1 and B7-DC uncouple costimulatory function from PD-1 interaction," *J Exp Med.*, 197(9):1083-1091, Epub Apr. 28, 2003.
Wang, "Lyophilization and development of solid protein pharmaceuticals," *Int J Pharm.*, 203(1-2):1-60, Aug. 10, 2000.
Wang, "pH-sensitive immunoliposomes mediate target-cell-specific delivery and controlled expression of a foreign gene in mouse," *Proc Natl Acad Sci U S A.*, 84(22):7851-7855, Nov. 1987.
Ward et al., "Binding activities of a repertoire of single immunoglobulin variable domains secreted from *Escherichia coli*," *Nature*, 341(6242):544-546, Oct. 12, 1989.
Webster et al., "Targeting molecular and cellular inhibitory mechanisms for improvement of antitumor memory responses reactivated by tumor cell vaccine," *J Immunol.*, 179(5):2860-2869, Sep. 1, 2007.
Weiss, "Hot Prospect for New Gene Amplifier: Ligase chain reaction, a combination DNA amplifier and genetic screen could do for DNA diagnostics what PCR has done for basic molecular biology," *Science*, 254(5036):1292-1293, Nov. 29, 1991.
Wherry et al., "Lineage relationship and protective immunity of memory CD8 T cell subsets," *Nat Immunol.*, 4(3):225-234, Epub Feb. 3, 2003.
Wick et al., "The hepatic immune system," *Crit Rev Immunol.*, 22(1):47-103, 2002.
Wilcox et al., "Provision of antigen and CD137 signaling breaks immunological ignorance, promoting regression of poorly immunogenic tumors," *J Clin Invest.*, 109(5):651-659, Mar. 2002.
Williams et al., "Introduction of foreign genes into tissues of living mice by DNA-coated microprojectiles," *Proc Natl Acad Sci U S A.*, 88(7):2726-2730, Apr. 1, 1991.
Williams et al., "The immunoglobulin superfamily—domains for cell surface recognition," *Annu Rev Immunol.*, 6:381-405, 1988.
Williams et al., "Nitric oxide synthase plays a signaling role in TCR-triggered apoptotic death," *J Immunol.*, 161(12):6526-6531, Dec. 15, 1998.
Willmore et al., "A novel DNA-dependent protein kinase inhibitor, NU7026, potentiates the cytotoxicity of topoisomemse II poisons used in the treatment of leukemia," *Blood*, 103(12):4659-4665, Epub Mar. 9, 2004.
Winter et al., "Man-made antibodies," *Nature*, 349(6307):293-299, Jan. 24, 1991.
Winter et al., "Making antibodies by phage display technology," *Annu Rev Immunol.*, 12:433-455, 1994.
Wintterle et al., "Expression of the B7-related molecule B7-H1 by glioma cells: a potential mechanism of immune paralysis," *Cancer Res.*, 63(21):7462-7467, Nov. 1, 2003.
Wofsy et al., "The proliferating cells in autoimmune MRL/lpr mice lack L3T4, an antigen on "helper" T cells that is involved in the response to class II major histocompatibility antigens," *J. Immunol.*, 132(6):2686-2689, Jun. 1984.
Wofsy, "Treatment of murine lupus with anti-CD4 monoclonal antibodies," *Immunol Ser.*, 59:221-236, 1993.
Wolff, "Direct gene transfer into mouse muscle in vivo," *Science*, 247(4949 Pt 1):1465-1468, Mar. 23, 1990.
Wong et al., "Human GM-CSF: molecular cloning of the complementary DNA and purification of the natural and recombinant proteins," *Science*, 228(4701):810-815, May 17, 1985.
Wu et al., The double-edged sword of activation-induced cytidine deaminase, *J Immunol.*, 174(2):934-941, Jan. 15, 2005.
Wu, "Receptor-mediated gene delivery and expression in vivo," *J Biol Chem.*, 263(29):14621-14624, Oct. 15, 1988.
Wu, "Targeting genes: delivery and persistent expression of a foreign gene driven by mammalian regulatory elements in vivo," *J Biol Chem.*, 264(29):16985-16987, Oct. 15, 1989.
Xu et al., "A potential new pathway for PD-L1 costimulation of the CD8-T cell response to Listeria monocytogenes infection," *PLoS One*, 8(2):e56539, Epub Feb. 11, 2013.
Xu et al., "The inducible expression of the tumor suppressor gene PTEN promotes apoptosis and decreases cell size by inhibiting the PI3K/Akt pathway in Jurkat T cells," *Cell Growth Differ.*, 13(7):285-296, Jul. 2002.
Yamamoto et al., "B7-H1 expression is regulated by MEK/ERK signaling pathway in anaplastic large cell lymphoma and Hodgkin lymphoma," *Cancer Sci.*, 100(11):2093-2100, Epub Aug. 1, 2009.
Yamazaki et al., "Expression of programmed death 1 ligands by murine T cells and APC," *J Immunol.*, 169(10):5538-5545, Nov. 15, 2002.
Yang et al., "In vitro priming of tumor-reactive cytolytic T lymphocytes by combining IL-10 with B7-CD28 costimulation," *J Immunol.*, 155(8):3897-3903, Oct. 15, 1995.
Yang et al., "In vivo and in vitro gene transfer to mammalian somatic cells by particle bombardment," *Proc Natl Acad Sci U S A.*, 87(24):9568-9572, Dec. 1990.
Yang, "Gene transfer into mammalian somatic cells in vivo," *Crit Rev Biotechnol.*, 12(4):335-356, 1992.
Yoshinaga et al., "T-cell co-stimulation through B7RP-1 and ICOS," *Nature*, 402(6763):827-832, Dec. 16, 1999.
Yotsumoto et al., "Endosomal translocation of CpG-oligodeoxynucleotides inhibits DNA-PKcs-dependent IL-10 production in macrophages," *J Immunol.*, 180(2):809-816, Jan. 15, 2008.
Youngnak et al., "Differential binding properties of B7-H1 and B7-DC to programmed death-1," *Biochem Biophys Res Commun.*, 307(3):672-677, Aug. 1, 2003.
Yuan et al., "Focus on histone variant H2AX: to be or not to b," *FEBS Lett.*, 584(17):3717-3724, Epub May 21, 2010.
Zang et al., "B7x: A widely expressed b7 family member that inhibits T cell activation," *Proc Natl Acad Sci U S A.*, 100(18):10388-10392, Epub Aug. 14, 2003.
Zang et al., "The B7 family and cancer therapy: costimulation and coinhibition," *Clin Cancer Res.*, 13(18 Pt 1):5271-5279, Sep. 15, 2007.
Zelenin et al., "Genetic transformation of mouse cultured cells with the help of high-velocity mechanical DNA injection," *FEBS Lett.*, 244(1):65-67, Feb. 13, 1989.
Zelenin et al., "High-velocity mechanical DNA transfer of the chlommphenicolacetyl transferase gene into rodent liver, kidney and mammary gland cells in organ explants and in vivo," *FEBS Lett.*, 280(1):94-96, Mar. 11, 1991.
Zhang et al., "Theiler's virus-infected L-selectin-deficient mice have decreased infiltration of CD8(+) T lymphocytes in central nervous system but clear the virus," *J Neuroimmunol.*, 116(2):178-187, Jun. 1, 2001.
Zhou et al., "Inducible-costimulator-mediated suppression of human immunodeficiency virus type 1 replication in CD4+ T lymphocytes," *Virology*, 325(2):252-263, Aug. 1, 2004.
Zou et al., "Inhibitory B7-family molecules in the tumour microenvironment," *Nat Rev Immunol.*, 8(6):467-477, Jun. 2008.
Zula et al., "The role of cell type-specific responses in IFN-β therapy of multiple sclerosis," *Proc Natl Acad Sci U S A.*, 108(49):19689-19694, Epub Nov. 21, 2011.
Zumla et al. "Granulomatous infections: etiology and classification," *Clin Infect Dis.*, 23(1):146-158, Jul. 1996.
Zwiebel et al., "Drug delivery by genetically engineered cell implants," *Ann N Y Acad Sci.*, 618:394-404, 1991.
European Search Report for Application No. EP 02802551, 3 pages, completed Oct. 14, 2004.
European Search Report for Application No. EP 14850189.3, dated Feb. 27, 2017, 5 pages.
International Preliminary Report on Patentability for PCT/US2014/053870, dated Apr. 5, 2016, 7 pages.
International Preliminary Report on Patentability in International Application No. PCT/US03/22029, dated Mar. 25, 2005, 5 pages.

(56) References Cited

OTHER PUBLICATIONS

International Preliminary Report on Patentability in International Application No. PCT/US07/060133, dated Oct. 30, 2008, 8 pages.
International Preliminary Report on Patentability in International Application No. PCT/US07/60150, dated Sep. 18, 2008, 5 pages.
International Preliminary Report on Patentability in International Application No. PCT/US2007/066970, dated Oct. 30, 2008, 8 pages.
International Preliminary Report on Patentability in International Application No. PCT/US2015/031993, dated Nov. 22, 2016, 11 pages.
International Preliminary Report on Patentability in International Application No. PCT/US2015/032016, dated Jan. 24, 2017, 11 pages.
International Preliminary Report on Patentability re PCT/US2009/035495, dated Sep. 10, 2010, 5 pages.
International Search Report and Written Opinion for PCT/US16/58852, dated Apr. 28, 2017, 15 pages.
International Search Report and Written Opinion for PCT/US2014/053870, dated Feb. 4, 2015, 12 pages.
International Search Report and Written Opinion for PCT/US2015/031993, dated Sep. 29, 2015, 18 pages.
International Search Report and Written Opinion for PCT/US2015/032016, dated Aug. 26, 2015, 17 pages.
International Search Report and Written Opinion in International Application No. PCT/US07/60133, dated Sep. 25, 2008, 13 pages.
International Search Report and Written Opinion in International Application No. PCT/US07/60150, dated Jul. 7, 2008, 8 pages.
International Search Report and Written Opinion in International Application No. PCT/US2007/066970, dated Oct. 5, 2007, 13 pages.
International Search Report and Written Opinion of the International Search Authority re PCT/US2009/035495, dated Oct. 6, 2009, 7 pages.
International Search Report for PCT/US2002/32364, dated Mar. 25, 2003, 2 pages.
International Search Report in International Application No. PCT/US03/22029, dated Dec. 2, 2004, 5 pages.
Invitation to Pay for PCT/US2014/053870, dated Nov. 19, 2014, 3 pages.
Supplementary European Search Report in International Application No. 03764649.4-2107, dated Oct. 6, 2006, 5 pages.
Dronca et al., "T cell Bim levels reflect responses to anti-PD-1 cancer therapy," *JCI Insight.*, 1(6):e86014, May 5, 2016, 14 pages.
Dronca et al., "BCL-2-interacting mediator of cell death (Bim) is a novel biomarker for response to anti-PD-1 therapy in patients with advanced melanoma," *Immunotherapy.*, 8(12)1351-1353, Dec. 1, 2016.
European Office Action in Application No. EP 14850189.3, dated Oct. 26, 2017, 11 pages.
Extended European Search Report in International Application No. 15825450.8, dated Feb. 21, 2018, 9 pages.

* cited by examiner

METHODS AND MATERIALS FOR TREATING CANCER

CROSS-REFERENCE TO RELATED APPLICATIONS

This application is a continuation of U.S. application Ser. No. 14/192,376, filed Feb. 27, 2014, (now U.S. Pat. No. 9,302,005), which claims the benefit of U.S. provisional application 61/786,199, filed Mar. 14, 2013. The disclosures of the prior applications are considered part of (and are incorporated by reference in) the disclosure of this application.

BACKGROUND

1. Technical Field

This document relates to methods and materials involved in treating cancer. For example, this document provides methods and materials for identifying a mammal as having an elevated level of CD8 T cells that express PD-1 and CD11a polypeptides (PD-1$^+$/CD11a$^{high}$ CD8 T cells) and administering a PD-1 inhibitor to such a mammal.

2. Background Information

CD11a (LFA-1, lymphocyte functional-associated antigen 1) is a polypeptide expressed by T cells. It binds to ICAM-1 on antigen-presenting cells and functions as an adhesion molecule. CD11a is indispensable in mediating conjugation of cytotoxic T lymphocytes (CTLs) and target cells. Blocking CD11a can dramatically reduce the killing of tumor cells and rejecting of transplants by CTLs.

B7-H1 is a polypeptide expressed by a variety of tumor cells. It also is constitutively expressed by macrophages and dendritic cells, its expression being up-regulated upon cell activation. PD-1 is a receptor for B7-H1 polypeptides.

SUMMARY

This document provides methods and materials involved in treating cancer. For example, this document provides methods and materials for identifying a mammal as having an elevated level of PD-1$^+$/CD11a$^{high}$ CD8 T cells having the potential to exert anti-cancer effects. In some cases, this document provides methods and materials for identifying a mammal as having an elevated level of PD-1$^+$/CD11a$^{high}$ CD8 T cells and administering a PD-1 inhibitor to such a mammal. Administration of a PD-1 inhibitor to a mammal having an elevated level of PD-1$^+$/CD11a$^{high}$ CD8 T cells can result in naturally-occurring tumor-reactive CD8 CTLs present within the PD-1$^+$/CD11a$^{high}$ CD8 T cell population exerting anti-cancer effects against cancer cells present within the mammal.

Having the ability to identify mammals with cancer that have an elevated level of PD-1$^+$/CD11a$^{high}$ CD8 T cells can allow clinicians to identify those cancer patients having the potential to exert anti-cancer effects against cancer cells present within the mammal. Once identified, a cancer patient having an elevated level of PD-1$^+$/CD11a$^{high}$ CD8 T cells can be administered a PD-1 inhibitor under conditions wherein naturally-occurring tumor-reactive CD8 CTLs present within the PD-1$^+$/CD11a$^{high}$ CD8 T cell population exert anti-cancer effects against cancer cells present within the mammal.

In general, one aspect of this document features a method for treating a mammal having cancer. The method comprises, or consists essentially of, (a) identifying the mammal as having an elevated level of PD-1$^+$/CD11a$^{high}$ CD8 T cells within a sample (e.g., a blood, body fluid, or tumor sample), and (b) administering a PD-1 inhibitor to the mammal under conditions wherein naturally-occurring tumor-reactive CD8 CTLs within a PD-1$^+$/CD11a$^{high}$ CD8 T cell population of the mammal are triggered to exert an anti-cancer effect against the cancer. The mammal can be a human. The elevated level can be determined using flow cytometry. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer.

In another aspect, this document features a method for treating cancer. The method comprises, or consists essentially of, administering a PD-1 inhibitor to a mammal identified as having an elevated level of PD-1$^+$/CD11a$^{high}$ CD8 T cells within a sample (e.g., a blood, body fluid, or tumor sample), wherein the PD-1 inhibitor is administered under conditions wherein naturally-occurring tumor-reactive CD8 CTLs within a PD-1$^+$/CD11a$^{high}$ CD8 T cell population of the mammal are triggered to exert an anti-cancer effect against the cancer. The mammal can be a human. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
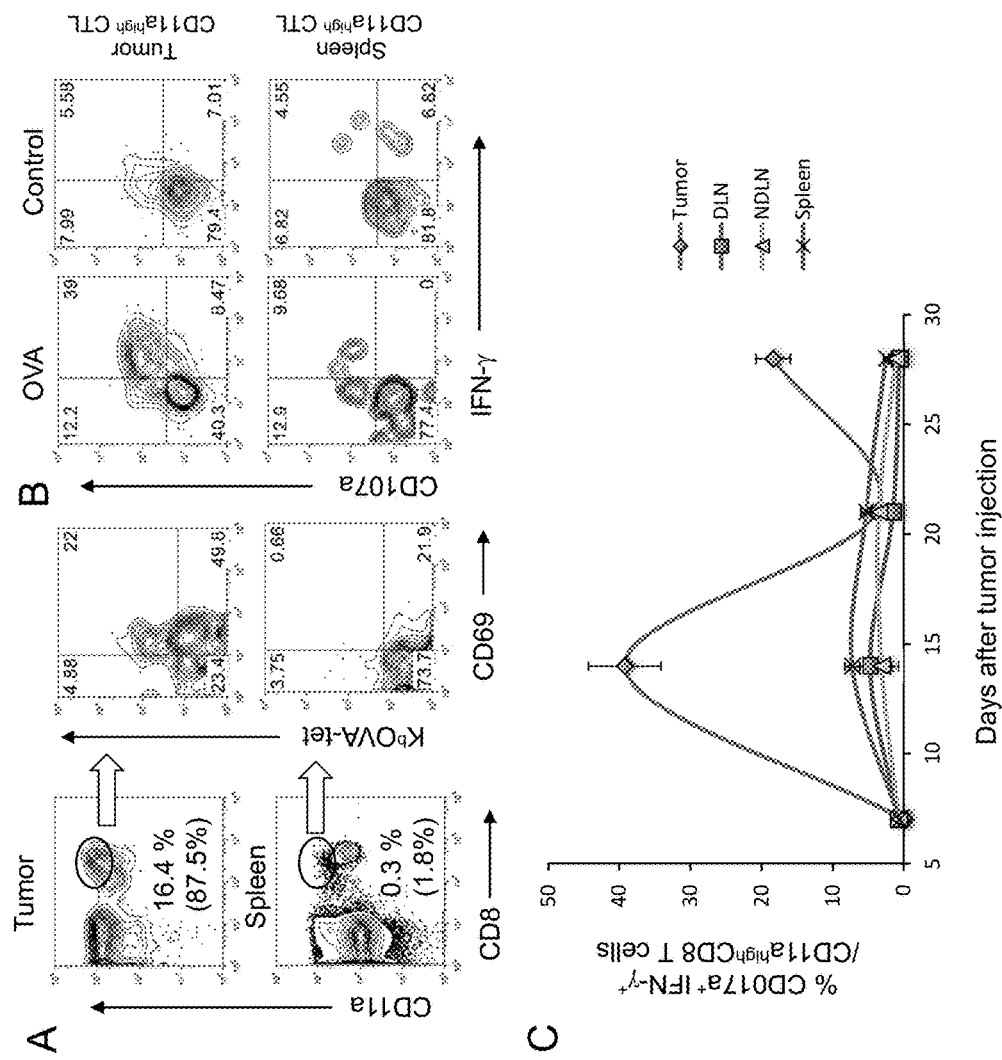
FIG. 1. Naturally-occurring tumor-specific CD8 T cells in tumor tissues. B16-OVA tumor cells were subcutaneously injected into naïve C57BL/6 mice. (A) On day 14 after tumor injection, lymphocytes were isolated from tumor tissues and spleen and were stained with antibodies for CD8, CD11a, CD69 and K$^b$OVA-tetramer. For measuring CTL activity, cells were incubated with OVA or control peptides for five hours in the presence of anti-CD107a antibody and followed by intracellular staining for IFN-γ. Data show the percentages of CD11a$^{high}$ CD8 T cells in whole tumor tissues and spleen. Percentages in parentheses indicate the percent of CD11a$^{high}$ subset per CD8 T cells. One of three independent experiments is shown. (B) The kinetics and distributions of functional CD11a$^{high}$ CD8 T cells in tumor tissues, draining lymph nodes (DLN) and non-draining lymph nodes (NDLN) and spleen. Data show the average percent±SD of CD107a$^+$ IFN-γ$^+$ per CD11a$^{high}$ CD8 T cells (n=3). (C) A graph plotting the percentage of the indicated cells vs. time post tumor injection.

This document provides methods and materials involved in treating cancer. For example, this document provides methods and materials for identifying a mammal as having an elevated level of PD-1$^+$/CD11a$^{high}$ CD8 T cells. As described herein, cancer patients having an elevated level of PD-1$^+$/CD11a$^{high}$ CD8 T cells can have an increased potential to exert anti-cancer effects. For example, cancer patients having an elevated level of PD-1$^+$/CD11a$^{high}$ CD8 T cells can have a population of naturally-occurring tumor-reactive CD8 CTLs with the capability of being triggered to exert anti-cancer effects against cancer cells present within the cancer patient.

The term "elevated level" as used herein with respect to a level of PD-1$^+$/CD11a$^{high}$ CD8 T cells refers to any level that is greater than a reference level of PD-1$^+$/CD11a$^{high}$ CD8 T cells. The term "reference level" as used herein with respect to PD-1$^+$/CD11a$^{high}$ CD8 T cells refers to the level of PD-1$^+$/CD11a$^{high}$ CD8 T cells typically observed in peripheral blood of healthy mammals without cancer. For example, a reference level of PD-1$^+$/CD11a$^{high}$ CD8 T cells can be the average number of PD-1$^+$/CD11a$^{high}$ CD8 T cells present in the peripheral blood obtained from a random sampling of 50 humans free of cancer. In some cases, an elevated level of PD-1$^+$/CD11a$^{high}$ CD8 T cells can be a level that is at least 10, 25, or 50 percent greater than a reference level of PD-1$^+$/CD11a$^{high}$ CD8 T cells.

In some cases, the presence of an elevated level of PD-1$^+$/CD11a$^{high}$ CD8 T cells can be determined using cell frequencies. For example, the presence of more than 20 PD-1$^+$/CD11a$^{high}$ CD8 T cells per 100 CD8 T cells within a peripheral blood sample can be an elevated level of PD-1$^+$/CD11a$^{high}$ CD8 T cells. It will be appreciated that levels from comparable samples are used when determining whether or not a particular level is an elevated level.

As described herein, the level of PD-1$^+$/CD11a$^{high}$ CD8 T cells present within a blood sample (e.g., a peripheral blood sample) can be used to determine whether or not a particular mammal has an increased potential to exert anti-cancer effects via CTLs. Any appropriate T cell-containing sample can be used as described herein to identify mammals having an elevated level of PD-1$^+$/CD11a$^{high}$ CD8 T cells. For example, tumor tissue samples, ascites samples, and lymphoid organ sample can be used to determine whether or not a mammal has an elevated level of PD-1$^+$/CD11a$^{high}$ CD8 T cells.

Any appropriate methods can be used to determine the level of PD-1$^+$/CD11a$^{high}$ CD8 T cells within a sample. For example, antibody staining techniques such an immunohistochemistry or flow cytometry can be used to determine whether or not a particular sample contains an elevated level of PD-1$^+$/CD11a$^{high}$ CD8 T cells.

Examples of anti-human PD-1 antibodies that can be used to identify PD-1$^+$/CD11a$^{high}$ CD8 T cells include, without limitation, anti-human PD-1 antibodies commercially available from Biolegend (Catalog Nos. 329904 or 329905; San Diego, Calif.) or eBioscience (Catalog No. 12-2799-42; San Diego, Calif.).

Examples of anti-human CD11a antibodies that can be used to identify PD-1$^+$/CD11a$^{high}$ CD8 T cells include, without limitation, anti-human CD11a antibodies commercially available from Biolegend (Catalog Nos. 301212 or 350604; San Diego, Calif.) or Novus (Catalog No. NB500-309; Littleton, Colo.).

Examples of anti-human CD8 antibodies that can be used to identify PD-1$^+$/CD11a$^{high}$ CD8 T cells include, without limitation, anti-human CD8 antibodies commercially available from BD Bioscience (Catalog No. 557851; San Jose, Calif.).

Examples of a human PD-1 nucleic acid can have the sequence set forth in GenBank® Accession No. BC074740.2 (GI No. 50960296), and a human PD-1 polypeptide can have the sequence set forth in GenBank® Accession No. AAH74740.1 (GI No. 49902307). Examples of a human CD11a nucleic acid can have the sequence set forth in GenBank® Accession No. BC008777.2 (GI No. 33870544), and a human CD11a polypeptide can have the sequence set forth in GenBank® Accession No. AAX29153.1 (GI No. 60652917).

Once the level (or frequency) of PD-1$^+$/CD11a$^{high}$ CD8 T cells within a sample from a mammal is determined, the level can be compared to a cut-off level, a cut-off frequency, or a reference level and used to classify the mammal as having or lacking an elevated level of PD-1$^+$/CD11a$^{high}$ CD8 T cells.

Once identified as having an elevated level of PD-1$^+$/CD11a$^{high}$ CD8 T cells as described herein, the mammal can be administered a PD-1 inhibitor. Examples of PD-1 inhibitors included, without limitation, anti-PD-1 antibodies, anti-PD-1 ligand antibodies, PD-1 fusion proteins, PD-1 siRNA, and PD-1 miRNA.

Administration of a PD-1 inhibitor to a mammal having an elevated level of PD-1$^+$/CD11a$^{high}$ CD8 T cells can result in naturally-occurring tumor-reactive CD8 CTLs present within the PD-1$^+$/CD11a$^{high}$ CD8 T cell population exerting anti-cancer effects against cancer cells present within the mammal.

In some cases, the presence of PD-1$^+$/CD11a$^{high}$ CD8 T cells in a cancer patient can represent a pre-existing immunity to cancer. In such cases, this population of T cells can represent a means to identify patients whose immune systems have already been primed by tumor antigens, yet are not able to exert an effective antitumor immunity. Such patients can be identified as described herein and can be treated with a PD-1 inhibitor to reduce the number of cancer cells present in that patient.

The invention will be further described in the following examples, which do not limit the scope of the invention described in the claims.

EXAMPLES

Example 1

B7-H1 Limits the Entry of Effector CD8$^+$ T Cells to the Memory Pool by Upregulating Bim In immunized B7-H1-deficient mice, an increased expansion of effector CD8$^+$ T cells and a delayed T cell contraction followed by the emergence of a protective CD8$^+$ T cell memory capable of completely rejecting tumor metastases in the lung were detected. Intracellular staining revealed that antigen-primed CD8$^+$ T cells in B7-H1-deficient mice express lower levels of the pro-apoptotic molecule Bim. The engagement of activated CD8$^+$ T cells by a plate-bound B7-H1 fusion protein led to the upregulation of Bim and increased cell death. Assays based on blocking antibodies determined that both PD-1 and CD80 are involved in the B7-H1-mediated regulation of Bim in activated CD8$^+$ T cells. See, also, Gibbons et al., *Oncoimmunology*, 1(7):1061-1073 (2012). These results suggested that B7-H1 negatively regulates CD8$^+$ T cell memory by enhancing the depletion of effector CD8$^+$ T cells through the upregulation of Bim.

Example 2

Natural Occurring Tumor-Reactive CD8 T Cells are Differentiated Effector Cells with High Expression of CD11a and PD-1

Mice, Cell Lines and Reagents

Female C57BL/6 and Balb/c mice were purchased from Taconic Farms (Germantown, N.Y.). PD-1 knockout (KO) C57BL/6 mice were obtained from L. Chen (Yale University, New Haven, Conn.) with the permission of Dr. T. Honjo (Kyoto University). Mice were maintained under pathogen-free conditions and used at 8-12 weeks of age. Tumor tissues and spleen samples from Balb-neuT mice were obtained from Dr. L. Pease (Mayo Clinic, Rochester). B16-OVA murine melanoma cells were obtained from R. Vile (Mayo Clinic, Rochester, Minn.), 4T1 tumor cells were purchased from ATCC and were cultured in RPMI 1640 medium (Cellgro, Hendon, Va.) with 10% FBS (Life Technologies, Carlsbad, Calif.), 1 U/mL penicillin, 1 μg/mL streptomycin, and 20 mM HEPES buffer (all from Mediatech, Manassas, Va.). FTY720 was obtained from Cayman Chemical (Ann Arbor, Mich.). PMA and Ionomycin were obtained from Sigma.

Flow Cytometry Analysis

Class I MHC (K$^b$OVA peptide: SIINFEKL (SEQ ID NO:1)) tetramer and control tetramer (mock-loaded) were obtained from Beckman Coulter (Brea, Calif.). Fluoro-chrome-conjugated Abs against CD3, CD8, CD11a (M17/4), CD69, PD-1, CD62L, T-bet, Foxp-3, Ki67, CD107a, and IFN-γ were obtained from BD Biosciences (Mountain View, Calif.), BioLegend (San Diego, Calif.), or eBioscience (San Diego, Calif.). To detect intracellular IFN-γ levels, cells were incubated with GolgiPlug (BD Biosciences) for four hours prior to analysis. Cells were stained for surface antigens and then incubated in Fixation Buffer (BioLegend) for 20 minutes at room temperature, followed by permeabilization using Permeabilization Wash Buffer (BioLegend). To detect the intranuclear levels of Ki67, T-bet, and Foxp 3, T cells were first stained for surface antigens (CD8 and CD11a), fixed, and then permeabilized by Foxp3 buffer kit according to the manufacture's protocol (eBioScience). After staining, cells were washed three times with washing buffer before analysis. At least 100,000 viable cells were live gated on FACScan or FACSCailbur (BD Biosciences, USA) instrumentation. Flow cytometry analysis was performed using FlowJo software (Tree Star, Ashland, Oreg.).

Cytotoxic T Lymphocyte (CTL) Function Assay

Degranulation of CTLs was measured by CD107a mobilization (Betts et al., *J. Immunol. Methods.*, 281:65-78 (2003)) followed by intracellular staining for IFN-γ. Briefly, lymphocytes were incubated with OVA peptide$_{257-264}$ (Mayo Clinic Peptide Core) at 1 μg/mL, or PMA (50 ng/mL)/Ionomycin (500 ng/mL) for four hours in the presence of anti-CD107a. After incubation, cells were stained for CD8 and CD11a followed by intracellular staining for IFN-γ.

Tumor Studies

Mice were inoculated subcutaneously or intravenously with 5×10$^5$ wild type or PD-1 KO B16-OVA tumor cells in C57BL/6 mice or 1×10$^5$ 4T1 tumor cells in BalB/c mice. A caliper was used to measure the length and width of tumors twice a week. Some mice were intraperitoneally injected with FTY720 (1 mg/kg) every two days over a week. On indicated days after tumor injection, tumor tissues and lymphoid organs were removed and incubated in digestion buffer (RPMI medium containing 5% fetal bovine serum, 0.02% Collagenase IV, 0.002% DNase I and 10 U/mL of Heparin) for 40 minutes followed with isolation of lymphocytes.

Detection of Melanoma Specific Human CD8 T Cells

Peripheral blood mononuclear cells (PBMC) samples were collected from HLA-A2 positive patients with stage IV melanoma. Cells were stained with antibodies for CD8, CD11a, PD-1 (MIH4), and CTLA-4 (BD Bioscience and eBioscience, Calif., USA). To detect melanoma antigen-specific CD8 T cells, PBMCs were stained with HLA-A2/MART-1 Tetramer (Beckman Coulter, Brea, Calif.).

Statistical Analysis

All statistical analyses were performed using GraphPad Prism software 5.0 (GraphPad Software, Inc., San Diego, Calif.). A two-sided, unpaired or paired Student T test was used to assess statistical differences in experimental groups. A p value <0.05 was considered statistically significant.

Results

CD11a$^{high}$ CD8 T Cells Form an Antitumoral T Cell Population

The presence of CD11a$^{high}$ CD8 T cells in mice harboring a subcutaneously growing tumor was monitored, and corresponding antigen-specific CTL function was analyzed. B16-OVA tumor cells which express a surrogate tumor antigen OVA (ovalbumin) were subcutaneously injected into naïve B6 mice. On day 7 after tumor injection, lymphocytes were isolated from tumor tissues, draining lymph nodes (DLN), non-draining lymph nodes (NDLN), and spleen. The expression of CD11a on CD8 T cells was examined by flow cytometry in freshly isolated lymphocytes from tumor or lymphoid tissues. CD11a$^{high}$ CD8 T cells were primarily detected within tumor tissue and were largely absent in the spleen, suggesting the accumulation of CD11a$^{high}$ CD8 T cells is tumor-associated (FIG. 1A). The antigen-specificity and activation status of CD11a$^{high}$ CD8 T cells were ascertained by staining using K$^b$OVA-tetramer and anti-CD69 antibody (FIG. 1A). Most tumor infiltrating CD11a$^{high}$ CD8 T cells within tumors were CD69 positive, and 54% of them were K$^b$OVA tetramer positive (FIG. 1A), while fewer spleen CD11a$^{high}$ CD8 T cells were K$^b$OVA tetramer positive even though a portion of them were CD69 positive. Cytotoxic T lymphocyte (CTL) capacity of CD11a$^{high}$ CD8 T cells was analyzed by measuring degranulation (CD107a expression) and IFN-γ production following a brief stimulation with OVA or control peptides ex vivo. CD11a$^{high}$ CD8 T cells from tumor site demonstrated degranulation and IFN-γ production following stimulation with OVA antigen peptide, but not with control peptide (FIG. 1B). In contrast, spleen CD11a$^{high}$ CD8 T cells exhibited weaker CTL function compared with tumor CD11a$^{high}$ CD8 T cells. These results suggested that CD11a$^{high}$ CD8 T cells are mainly identified within tumors and that they are effector CTLs responding to specific tumor antigens.

Tracking the kinetics and distribution of CD11a$^{high}$ CD8 T cells in tumor-bearing host, functional (CD107a$^+$ IFN-γ$^+$) CD11a$^{high}$ CD8 T cells were determined to peak within tumors on day 14 after tumor injection and progressively diminished in frequency over the next seven day (FIG. 1C). Interestingly, functional CD11a$^{high}$ CD8 T cells increased in numbers thereafter as the tumor grew, and the mice euthanized at day 28 (FIG. 1C). In contrast, functional CD11a$^{high}$ CD8 T cells were barely found in tumor-draining lymph nodes (DLN), non-DLN, and spleen from day 7 through day 28 after tumor injection. These results led to the conclusion that CD11a$^{high}$ CD8 T cells represent tumor-specific and tumor-reactive functional CD8 CTLs in tumor sites.

Figure 2:
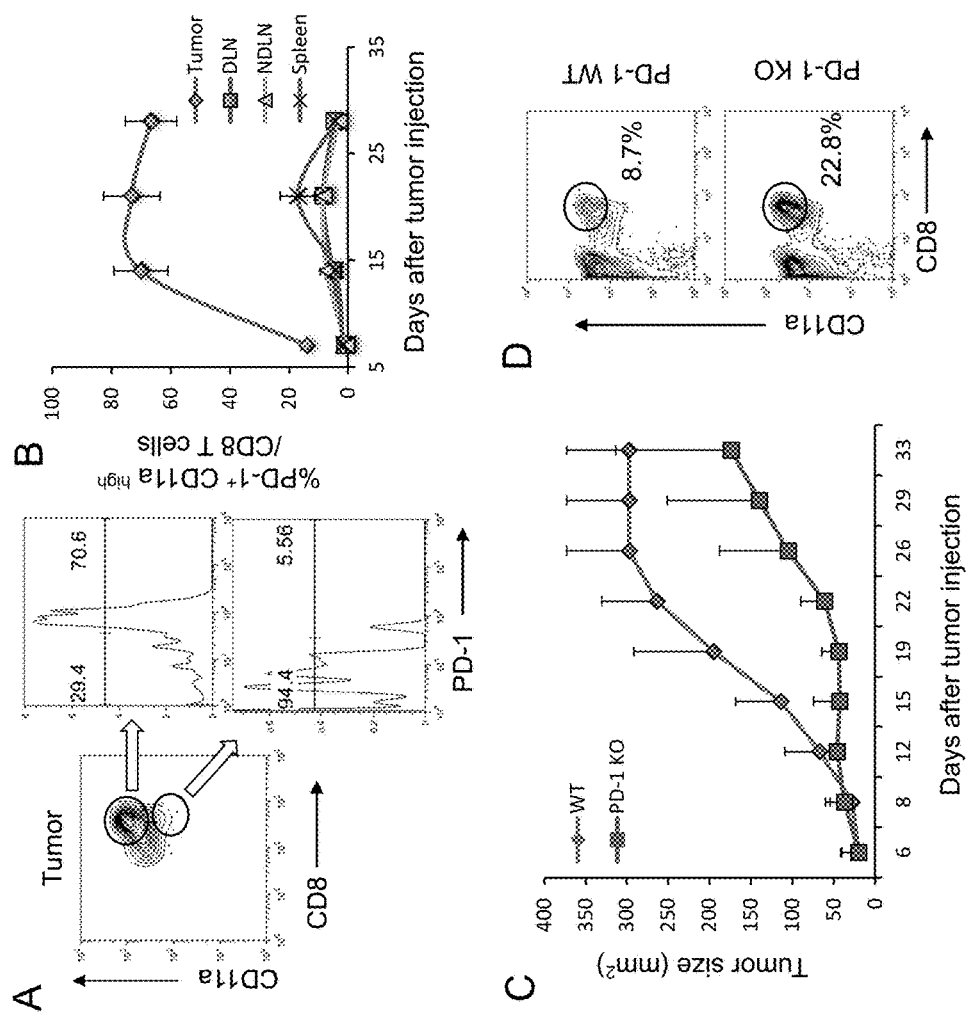
FIG. 2. PD-1 limits the natural antitumor immunity. (A) PD-1 expression by CD11a$^{high}$ CD8 T cells isolated from subcutaneously implanted B16-OVA tumors. (B) Kinetics and distribution of PD-1$^+$ CD11a$^{high}$ CD8 T cells in tumor tissues, draining lymph nodes (DLN) and non-draining lymph nodes (NDLN) and spleen. (C) Subcutaneous implanted B16-OVA tumor growth in wild type (WT) and PD-1 knockout (KO) mice. Data show the mean size of tumors plus SD (n=4). (D) Percentages of CD11a$^{high}$ CD8 T cells in tumor tissues on day 12 after tumor injection in WT and PD-1 KO mice.

High Expression of PD-1 by CD11a$^{high}$ CD8 T Cells Compromises the Ability to Control Tumor Growth Although functional tumor-reactive CD11a$^{high}$ CD8 T cells were identified within tumors, they were unable to control tumor growth. Several factors could contribute to compromised anti-tumoral activity including the possibility that T cells might become exhausted following chronic antigen exposure within the tumor bed. To examine this scenario, the expression of PD-1, an immunoregulatory receptor expressed by exhausted T cells (Barber et al., Nature, 439:682-687 (2006)) and tumor-associated T cells (Thompson et al., Clinical Cancer Research, 13:1757-1761 (2007); Zhang et al., Blood, 114:1545-1552 (2009); Mumprecht et al., Blood, 114:1528-1536 (2009); and Ahmadzadeh et al., Blood, 114:1537-1544 (2009)), on CD11a$^{high}$ CD8 T cells isolated from tumors was determined. CD11a$^{high}$ CD8 T cells isolated from established tumors expressed elevated levels of PD-1 compared to naïve CD8 T cells (FIG. 2A). In contrast, CD11a$^{low}$ CD8 T cells did not express PD-1. The expression of PD-1 was first detected on CD11a$^{high}$ CD8 T cells isolated from day 7 tumors and maintained within tumors until day 28 (FIG. 2B). To test whether the quick and persistent expression of PD-1 by CD11a$^{high}$ CD8 T cells impairs the antitumor activity of tumor-reactive CD11a$^{high}$ CD8 T cells, B16-OVA tumor cells were injected into naïve PD-1 KO mice, and tumor growth was measured. B16-OVA growth was significantly delayed in PD-1 KO mice compared to WT mice (FIG. 2C). These results indicated that PD-1 negatively regulates natural antitumor immunity. To ascertain whether increased natural antitumor immunity is related to the presence of CD11a$^{high}$ CD8 T cells, the frequencies of CD11a$^{high}$ CD8 T cells within tumors established in PD-1 KO mice and wild-type mice on day 12, when their tumors grew to the same size, were measured. Interestingly, CD11a$^{high}$ CD8 T cells increased 2-3 fold within tumors in PD-1 KO mice compared with wild type mice (FIG. 2D). These results suggested that tumor-reactive CD11a$^{high}$ CD8 T cells are functional but are compromised in their capacity to control tumor growth due to high and persistent expression of PD-1.

Tumor-Induced CD11a$^{high}$ CD8 T Cells are Present at Primary and Metastatic Tumor Sites Tumor-specific, functional CD11a$^{high}$ CD8 T cells were identified using a tumor model with a surrogate tumor antigen. To extend this observation to a tumor antigen undefined system and to detect tumor-reactive CD8 T cells at primary and secondary (metastatic) tumor sites, an antigen undefined mouse breast tumor (4T1) was used, which develops a tumor after subcutaneously injection and forms metastasis (preferentially in the lung) after intravenous infusion. The frequency of CD11a$^{high}$ CD8 T cells within subcutaneously inoculated 4T1 tumors was examined first. The frequency of CD11a$^{high}$ CD8 T cells within 4T1 tumors exhibited similar kinetics as was observed for B16-OVA tumors.

Figure 3:
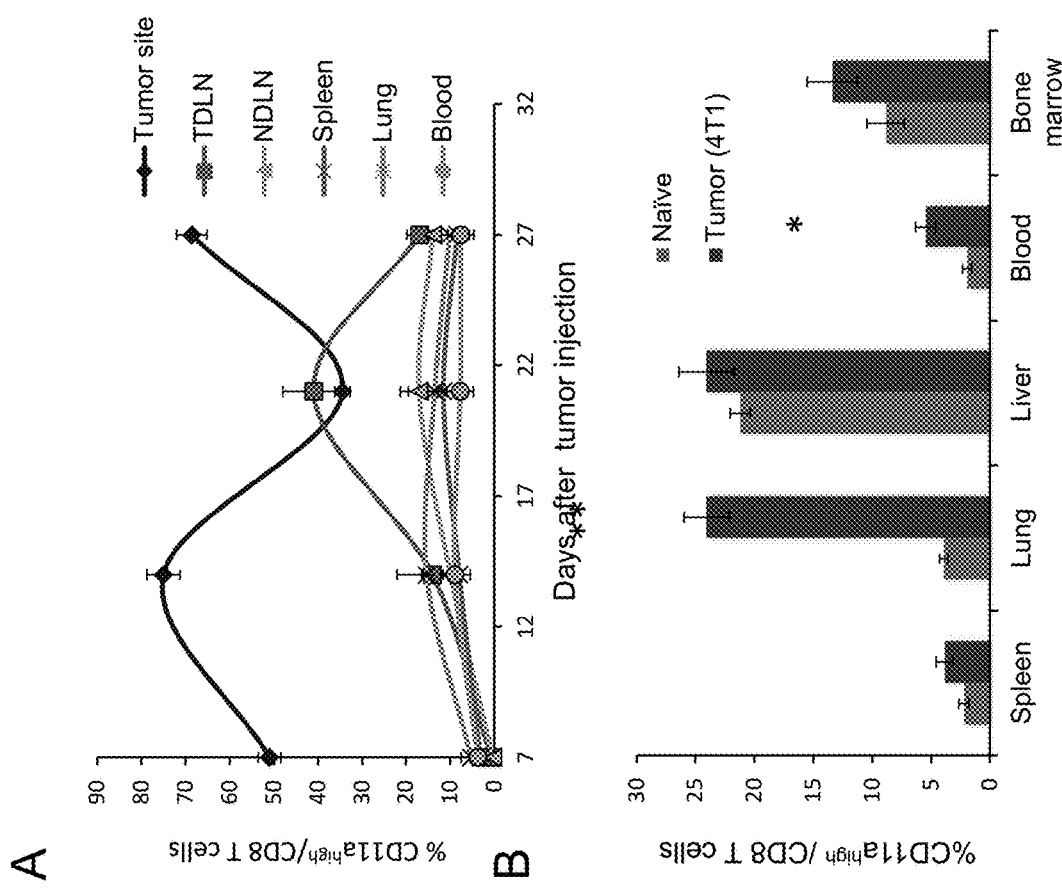
FIG. 3. CD11a$^{high}$ CD8 T cells identified at primary and metastatic tumor sites. 4T1 mouse breast tumor cells (1×10$^5$) were injected subcutaneously (A) or intravenously (B). (A) The kinetics and distribution of CD11a$^{high}$ CD8 T cells in multiple tissues of mice with primary subcutaneously implanted 4T1 tumors. TDLN, tumor draining lymph nodes, NDLN, non-draining lymph nodes. (B) The distribution of CD11a$^{high}$ CD8 T cells in multiple tissues of naive mice and mice with 4T1 tumors on day 7 after intravenously tumor injection. *p<0.05, **p<0.01 compared with naïve mice. Three mice per group, one of three experiments is shown.

CD11a$^{high}$ CD8 T cells were first detectable on day 7 after tumor injection, increasing within 4T1 tumors towards day 14, and declining thereafter. As with the B16-OVA system, CD11a$^{high}$ CD8 T cells increased in frequency from days 21-27 (FIG. 3A). CD11a$^{high}$ CD8 T cells only transiently appeared in draining lymph nodes on day 21 following tumor injection and did not appreciably populate in spleen, lung, or peripheral blood (FIG. 3A).

To detect whether CD11a$^{high}$ CD8 T cells were induced at the metastatic sites of 4T1 tumors, lymphocytes were isolated and analyzed from multiple organs after intravenously infusion of 4T1 tumor cells, a model of systemic tumor metastasis. On day 7 after tumor infusion, the number of CD11a$^{high}$ CD8 T cells significantly increased in the lung (22.7% of CD8 T cells, p<0.01) and in blood (3.9% of CD8 T cells, p<0.05), but the numbers were unchanged in the spleen, liver, and bone marrow compared with naïve mice (FIG. 3B). Unexpectedly, the largest percentages of CD11a$^{high}$ CD8 T cells were observed in livers from tumor bearing or naïve mice. As the liver is a main location for deposition and depletion of naturally or endogenously activated CD8 T cells (Crispe, Immunology, 3:51-62 (2003); and Dong et al., Immunity, 20:327-336 (2004)), the accumulation of CD11a$^{high}$ CD8 T cells in the liver suggested that CD11a$^{high}$ CD8 T cells are representative of antigen-primed T cell population.

Figure 4:
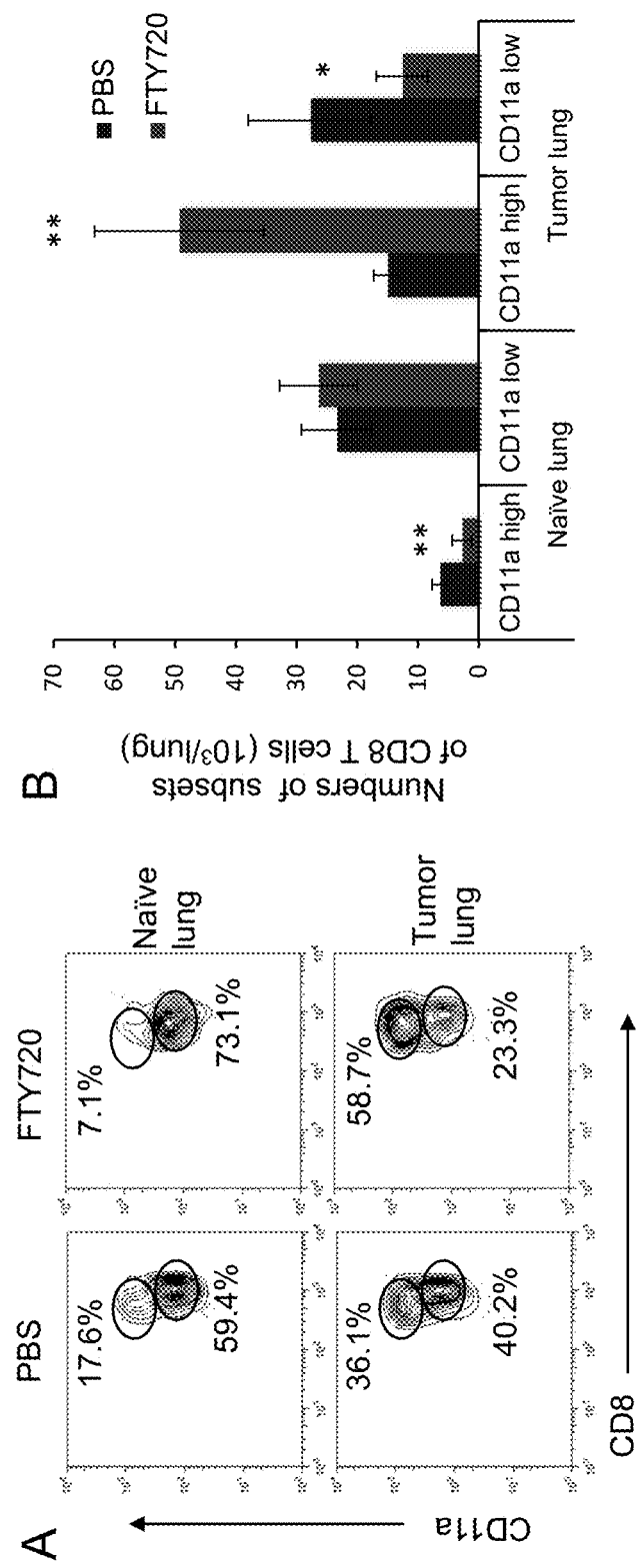
FIG. 4. In situ expansion of CD11a$^{high}$ CD8 T cells within tumor site. 4T1 tumor cells were intravenously injected into Balb/c mice with or without intraperitoneal injection of 1 mg/kg of FTY720. On day 7 after tumor injection, lymphocytes were isolated from the lung of tumor mice and naïve mice that also received FTY720. (A) Percentages of CD11a$^{high}$ and CD11a$^{low}$ CD8 T cells in the lungs. (B) Absolute numbers (mean±SD) of CD11a$^{high}$ and CD11a$^{low}$ CD8 T cells in the lung (n=3). *p=0.022,**p=0.013 compared with control PBS groups. One of two independent experiments is shown.

To ascertain whether CD11a$^{high}$ CD8 T cells represent in situ tumor induction or reflect a migratory influx following activation from other tumor bearing sites, FTY720, a molecule known to inhibit lymphocyte emigration from lymphoid organs (Brinkmann et al., Transplantation, 72:764-769 (2001)), was injected following infusion of tumor cells. After injection of FTY720 with or without tumor cells, the frequencies of CD11a$^{high}$ CD8 T cells in the lung of naïve mice and tumor-bearing mice were measured and compared. In naïve mice, FTY720 blocked the accumulation of CD11a$^{high}$ CD8 T cells in both frequency and numbers, but not CD11a$^{low}$ CD8 T cells, in the lung (FIG. 4), suggesting that CD11a$^{high}$ CD8 T cells may have an origin in lymphoid organs. However, in tumor-bearing mice, FTY720 did not block the accumulation of CD11a$^{high}$ CD8 T cells in the lung (FIG. 4). Unexpectedly, both the frequency and numbers of CD11a$^{high}$ CD8 T cells increased in the lung after FTY720 injection. According to the decrease of CD11a$^{low}$ CD8 T cells in the lung of tumor mice after FTY720 injection, the increase of CD11a$^{high}$ CD8 T cells suggested that the majority of resident rather than migrated naïve CD11a$^{low}$ CD8 T cells are induced by tumor cells to become CD11a$^{high}$ CD8 T cells that are undergoing expansion in the lung.

Figure 5:
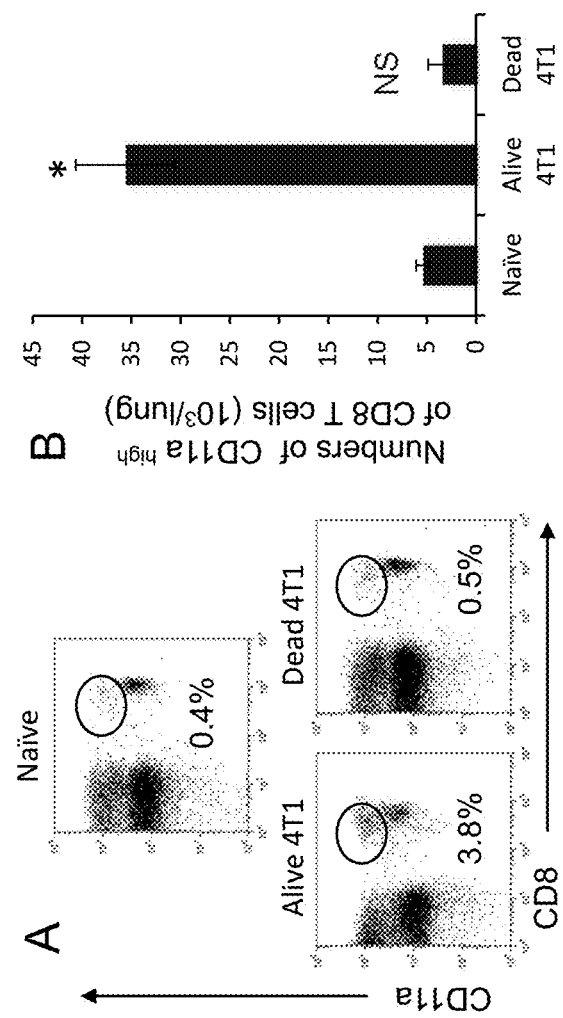
FIG. 5. Live tumor cells induce CD11a$^{high}$ CD8 T cell responses. Alive or lethally irradiated 4T1 tumor cells (loss of ability to infiltrate target tissues) were intravenously injected into naïve Balb/c mice. On day 7 after tumor injection, lymphocytes were isolated from the lungs of tumor mice or naïve control mice. (A) The percentages of CD11a$^{high}$ CD8 T cells in the lung (target tissues). (B) Absolute numbers (mean±SD) of CD11a$^{high}$ CD8 T cells in the lung (n=3). *p=0.0004, NS (non-significant) compared with naive groups. One of two independent experiments is shown.

To further confirm that the active infiltration of 4T1 tumor cells is driving CD8 T cell activation, either lethally irradiated 4T1 tumor cells, which have lost the ability to infiltrate tissues, or viable 4T1 tumor cells were intravenously injected into naïve mice. On day 7 after tumor injection, CD11a$^{high}$ CD8 T cells increased in the lungs of mice injected with live 4T1 tumor cells, but not in the lungs of mice infused with dead 4T1 tumor cells (FIG. 5). Thus, it was concluded that CD11a$^{high}$ CD8 T cells are local T cells responding to active infiltration of tumor cells at both primary and metastatic tumor sites.

Figure 6:
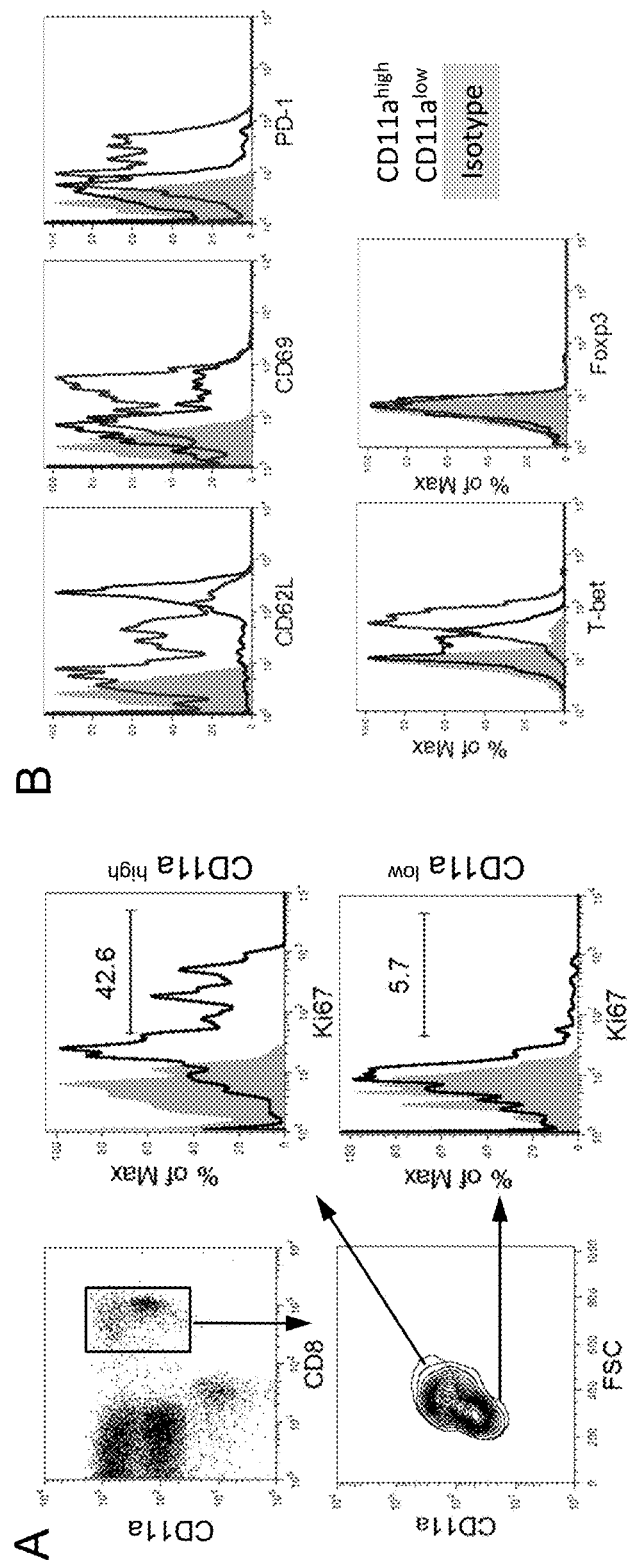
FIG. 6. Phenotype of tumor-induced CD11a$^{high}$ CD8 T cells. Lymphocytes were isolated from the lung of mice on day 7 after intravenously injection of 4T1 tumor cells. (A) Proliferation of CD11a$^{high}$ CD8 T cells measured by their larger forward light scatter (FSC) and intranuclear expression of Ki67. (B) Surface expression of CD62L, CD69 and PD-1 and intracellular expression of T-bet and Foxp3 by CD11a$^{high}$ and CD11a$^{low}$ CD8 T cells. One of three independent experiments is shown.
Figure 7:
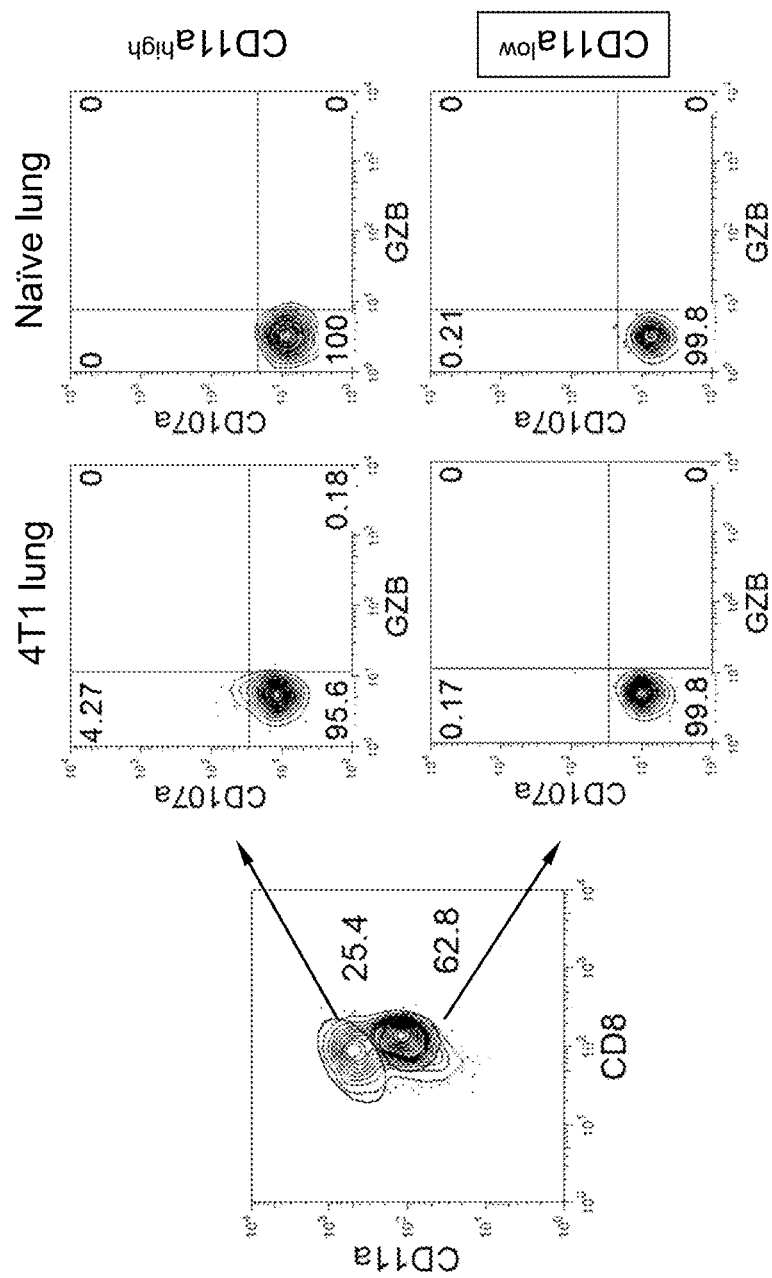
FIG. 7. Function of CD11a$^{high}$ CD8 T cells within 4T1 tumor tissues. Lymphocytes were isolated from the lung of naïve mice or mice on day 7 after intravenous injection of 4T1 tumor cells. CTL function of CD11a$^{high}$ or CD11a$^{high}$ CD8 T cells was assessed by measuring degranulation (CD107a expression) and intracellular production of IFN-gamma following a 4-hour ex vivo stimulation with PMA/ionomycin. One of three independent experiments is shown.

Poor Immunogenic Tumor-Induced CD11a$^{high}$ CD8 T Cells are Proliferative Effector Cells but Lack of Robust CTL Function The accumulation of CD11a$^{high}$ CD8 T cells at both primary and metastatic sites of 4T1 tumor was striking because the 4T1 tumor is postulated to be a poorly immunogenic tumor (Lewis et al., Cancer Research, 65:2938-2946 (2005)). The following was performed to analyze the phenotype and function of CD11a$^{high}$ CD8 T cells isolated from 4T1 tumor tissues. CD11a$^{high}$ CD8 T cells were proliferative cells in that the cells were large blasts (larger forward light scatter in flow cytometry) and expressed Ki67, a nuclear protein linked to cell proliferation (FIG. 6A). Phenotype analysis (FIG. 6B) revealed that CD11a$^{high}$ CD8 T cells were activated T cells (CD62L$^{low}$, CD69$^{high}$, PD-1$^{high}$). CD11a$^{high}$ CD8 T cells expressed higher levels of transcriptional factor T-bet that determines the differentiation of Th1 or CTLs (Harrington et al., J. Exp. Med., 191:1241-1246 (2000)), but did not express Foxp3, a master factor for T regulatory cells (FIG. 6B), suggesting that CD11a$^{high}$ CD8 T cells underwent effector differentiation. To examine whether the cells acquired effector function, degranulation (CD107a expression) and granzyme B (an executive molecule of CTL) expression by CD11a$^{high}$ CD8 T cells induced by 4T1 tumors in the lung were measured. Because the tumor antigens are not defined in 4T1 tumor cells, phorbol myristate acetate (PMA)/ionomycin, which bypasses TCR signaling, were used to activate T cell by activating DAG and calcium release (Truneh et al., Nature, 313:318-320 (1985)). Compared with CD8 T cells from naïve mice, tumor-induced CD11a$^{high}$ CD8 T cells slightly increased CD107a expression, but did not produce granzyme B (FIG. 7). These results suggested that CD11a$^{high}$ CD8 T cells induced by poorly immunogenic tumors are proliferative differentiated effector cells that lack robust CTL function.

CD11a$^{high}$ CD8 T Cells are Induced by Spontaneous Tumors

Figure 8:
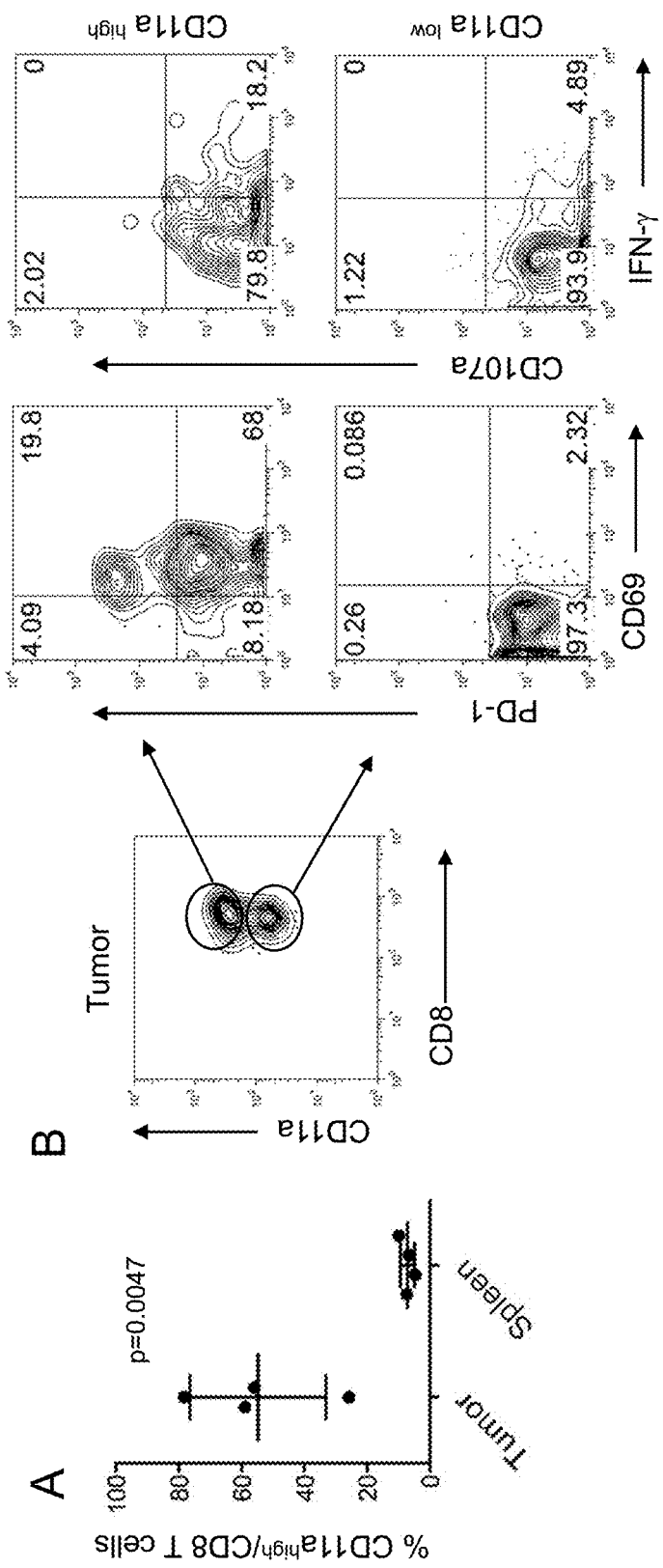
FIG. 8. CD11a$^{high}$ CD8 T cells identified within spontaneous tumors. Lymphocytes were isolated from the breast tissues with tumors or spleen of Blab-neuT mice at 15-18 weeks of age. (A) Percentage of CD11a$^{high}$ CD8 T cells within tumors and spleen. (B) Phenotype and function of CD11a$^{high}$ and CD11a$^{low}$ CD8 T cells isolated from tumor tissues. Degranulation (CD107a expression) and IFN-γ pro- duction were measured following a 4-hour ex vivo stimulation with PMA/ionomycin. One of three independent experiments is shown.

Although up-regulation of CD11a on CD8 T cells is not affected by inflammation (Rai et al., J. Immunol., 183:7672-7681 (2009)), the injected tumor cells may cause acute CD8 T cell responses to large tumor antigen exposure leading to accumulation of CD11a$^{high}$ CD8 T cells at the tumor site. As spontaneous tumors provide chronic and persistence antigen exposure for CD8 T cells, it was important to determine if it would be possible to detect accumulation of CD11a$^{high}$ CD8 T cells within spontaneous tumors. Lymphocytes were isolated from spontaneous breast tumors generated in female Balb-neuT mice carrying the activated HER-2/neu oncogene (Boggio et al., J. Exp. Med., 188:589-596 (1998)). At 17-20 weeks of age when the mammary glands display visible invasive carcinoma (Nava-Parada et al., Cancer Research, 67:1326-1334 (2007)), a significant increase of CD11a$^{high}$ CD8 cells within tumor tissues, but not in spleen, of the same host was measured (FIG. 8A). In addition, CD11a$^{high}$ CD8 T cells expressed high levels of CD69 and PD-1 (FIG. 8B). Functionally, spontaneous tumor-induced CD11a$^{high}$ CD8 T cells slightly increased IFN-γ production, but did not express CD107a after ex vivo stimulation with PMA/ionomycin (FIG. 8C). But, their CTL function could not be induced by a high affinity Neu antigen peptide (p66) (Nava-Parada et al., Cancer Research, 67:1326-1334 (2007)). As CD69 is a recent T cell activation maker and PD-1 is a marker of T cell exhaustion, these results suggested diversity among CD11a$^{high}$ CD8 T cells, reflecting the presence of both recently activated and exhausted T subpopulations. The dysfunction of these two populations was consistent with their failure in control the growth of spontaneous tumors.

Figure 9:
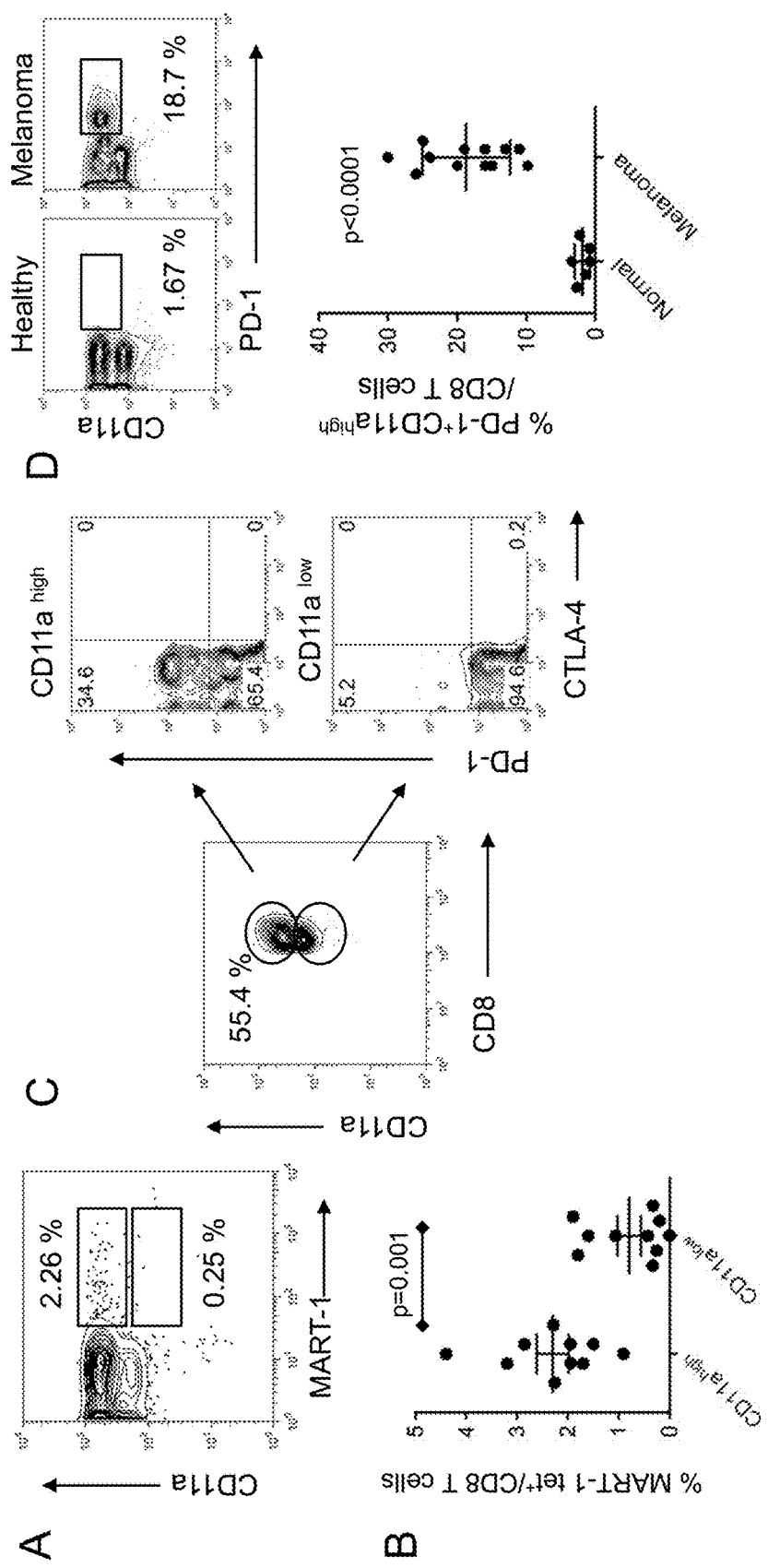
FIG. 9. PD-1$^+$ CD11a$^{high}$ CD8 T cells increased in the peripheral blood of melanoma patients. Peripheral blood mononuclear cells (PBMCs) were isolated from healthy donors or patients with stage IV melanoma. (A) Tumor antigen specificity of CD11a$^{high}$ CD8 T cells in PBMCs of melanoma patients. Numbers are the percent of MART-1 tet$^+$ in CD11a$^{high}$ and CD11a$^{low}$ CD8 T cells. (B) Percentages of MART-1-tee CD11a$^{high}$ and MART-1-tet$^+$ CD11a$^{low}$ cells in total CD8 T cells. Data show mean±SEM, n=10. (C) Expression of PD-1 and CTLA-4 by CD11a$^{high}$ and CD11a$^{low}$ CD8 T cells of PBMCs from melanoma patients. (D) Frequency of PD-1$^+$ CD11a$^{high}$ per total CD8 T cells in PBMCs of healthy donors (n=6) and melanoma patients (n=12).

Tumor-Reactive PD-1$^+$ CD11a$^{high}$ CD8 T Cells Increased in the Blood of Melanoma Patients To test whether CD11a$^{high}$ CD8 T cells consist of tumor specific CD8 T cells in cancer patients, CD8 T cells were analyzed from ten patients with stage IV melanoma. To define tumor-specific CD8 T cells, human CD8 T cells from melanoma patients were co-stained with HLA-A2/MART-1 tetramer detecting MART-1 (a melanoma differentiation antigen)-specific CD8 T cells. More Mart-1-specific T cells were identified in CD11a$^{high}$ subset of CD8 T cells than in CD11a$^{low}$ subsets (FIGS. 9A and 9B), suggesting that CD11a$^{high}$ CD8 T cells consist of tumor-specific CD8 T cells. Analyzing the expression of immunoregulatory receptors (PD-1 and CTLA-4), it was determined that CD11a$^{high}$ CD8 T cells expressed elevated levels of PD-1, but not CTLA-4, compared with CD11a$^{low}$ CD8 T cells (FIG. 9C). In comparison with healthy donors, the frequency of PD-1$^+$ CD11a$^{high}$ CD8 T cells significantly increased in the peripheral blood of patients with stage IV melanoma (18.7±1.8% vs. 1.7±0.4% of healthy donor, p<0.0001, FIG. 9D). At this advanced stage of melanoma, accumulation of PD-1$^+$ CD8 T cells may reflect the dysfunctional state of tumor-reactive CD8 T cells in these patients. These results suggested that in melanoma patients, most of the tumor specific CD8 T cells are CD11a$^{high}$ CD8 T cells that co-express elevated levels of PD-1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for exerting anti-cancer effects in a mammal having cancer, wherein said method comprises:
   (a) identifying said mammal as having an elevated level of PD-1+/CD11a$^{high}$ CD8 T cells within a T cell-containing sample; relative to a reference level of PD-1$^+$/CD11a$^{high}$ CD8 T cells in mammals without cancer; and
   (b) administering a PD-1 inhibitor to said mammal under conditions wherein naturally occurring tumor-reactive CD8 CTLs within a PD-1+/CD11a$^{high}$ CD8 T cell population of said mammal exert said anti-cancer effects against said cancer.

2. The method of claim 1, wherein said mammal is a human.

3. The method of claim 1, wherein said elevated level is determined using flow cytometry.

4. The method of claim 1, wherein said cancer is a melanoma cancer, a breast cancer, a lung cancer, a renal cell carcinoma cancer, a pancreas cancer, a prostate cancer, a colon cancer, a brain cancer, a liver cancer, or an ovarian cancer.

5. The method of claim 1, wherein said T cell-containing sample is a blood, body fluid, or tumor sample.

6. The method of claim 5, wherein said T cell-containing sample is a blood sample, and wherein said blood sample is a peripheral blood sample.

7. A method for exerting anti-cancer effects in a mammal having cancer, wherein said method comprises administering a PD-1 inhibitor to a mammal identified as having an elevated level of PD-1+/CD11a$^{high}$ CD8 T cells within a T cell-containing sample relative to a reference level of PD-1+/CD11a$^{high}$ CD8 T cells in mammals without cancer; wherein naturally occurring tumor-reactive CD8 CTLs within a PD-1+/CD11a$^{high}$ CD8 T cell population of said mammal exert said anti-cancer effects against said cancer.

8. The method of claim 7, wherein said mammal is a human.

9. The method of claim 7, wherein said elevated level is determined using flow cytometry.

10. The method of claim 7, wherein said cancer is a melanoma cancer, a breast cancer, a lung cancer, a renal cell carcinoma cancer, a pancreas cancer, a prostate cancer, a colon cancer, a brain cancer, a liver cancer, or an ovarian cancer.

11. The method of claim 7, wherein said T cell-containing sample is a blood, body fluid, or tumor sample.

12. The method of claim 11, wherein said T cell-containing sample is a blood sample, and wherein said blood sample is a peripheral blood sample.

* * * * *

UNITED STATES PATENT AND TRADEMARK OFFICE
CERTIFICATE OF CORRECTION

PATENT NO. : 10,167,336 B2
APPLICATION NO. : 15/054385
DATED : January 1, 2019
INVENTOR(S) : Haidong Dong et al.

Page 1 of 1

It is certified that error appears in the above-identified patent and that said Letters Patent is hereby corrected as shown below:

In the Specification

Column 1, Line 8, delete "2014," and insert -- 2014 --;

In the Claims

Column 11, Line 36, Claim 1, delete "sample;" and insert -- sample --;

Column 11, Lines 39-40, Claim 1, after "mammal" delete "under conditions".

Signed and Sealed this
Thirtieth Day of June, 2020

Andrei Iancu
*Director of the United States Patent and Trademark Office*